United States Patent
Bondinell et al.

[11] Patent Number: 6,008,213
[45] Date of Patent: Dec. 28, 1999

[54] INTEGRIN RECEPTOR ANTAGONISTS

[75] Inventors: William E. Bondinell, Wayne; William H. Miller, Schwenksville, both of Pa.

[73] Assignee: SmithKline Beecham Corporation, Philadelphia, Pa.

[21] Appl. No.: 08/722,095

[22] PCT Filed: Jun. 28, 1996

[86] PCT No.: PCT/US96/11108

§ 371 Date: Dec. 19, 1997

§ 102(e) Date: Dec. 19, 1997

[87] PCT Pub. No.: WO97/01540

PCT Pub. Date: Jan. 16, 1997

Related U.S. Application Data

[60] Provisional application No. 60/000,665, Jun. 29, 1995.

[51] Int. Cl.[6] .............. C07D 235/04; C07D 235/06; C07D 211/06; C07D 213/02

[52] U.S. Cl. .............. 514/211; 514/215; 514/217; 514/316; 514/352; 540/547; 540/550; 540/557; 540/587; 540/588; 546/187; 546/285; 548/304.4; 548/309.7

[58] Field of Search ................... 514/211, 215, 514/217, 316, 352; 540/547, 550, 557, 587, 588; 546/187, 285; 548/304.4, 309.7

[56] References Cited

U.S. PATENT DOCUMENTS

| | | | |
|---|---|---|---|
| 3,906,040 | 9/1975 | Vincent et al. | 260/558 R |
| 3,972,936 | 8/1976 | Christy | 260/570.8 T |
| 5,302,602 | 4/1994 | Oshima et al. | 514/325 |
| 5,726,192 | 3/1998 | Bondinell et al. | 514/352 |
| 5,756,519 | 5/1998 | Bondinell et al. | 514/316 |

FOREIGN PATENT DOCUMENTS

WO 98/15278  4/1998  WIPO.

*Primary Examiner*—Richard L. Raymond
*Assistant Examiner*—Deepak R. Rao

*Attorney, Agent, or Firm*—Mary E. McCarthy; Stephen Venetianer; Charles M. Kinzig

[57] ABSTRACT

Compounds of formula (I)

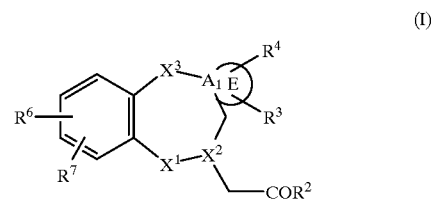

(I)

wherein $A_1$ is C or N; E is a five- or six-membered heteroaromatic or six-membered aromatic ring optionally substituted by $R^3$ or $R^4$; $X^1$—$X^2$ is $CHR^1$—CH, $CR^1$=CH, $NR^1$—CH, $S(O)_u$—CH or O—CH; $X^3$ is $CR^{5}R^{5'}$, $NR^5$, $S(O)_u$ or O; $R^2$ is —OR', —NR'R", —NR'SO$_2$R'", —NR'OR', —OCR'$_2$C(O)OR', —OCR'$_2$OC(O)—R', —OCR'$_2$C(O)NR'$_2$, $CF_3$ or —COCR'$_2$R$^{2'}$; $R^3$, $R^4$ and $R^7$ are independently H, halo, —OR$^{12}$, —SR$^{12}$, —CN, —NR'R$^{12}$, —NO$_2$, —CF$_3$, CF$_3$S(O)$_r$—, —CO$_2$R', —CONR'$_2$, $R^{14}$—C$_{0-6}$alky-, $R^{14}$—C$_{1-6}$oxoalkyl-, $R^{14}$—C$_{2-6}$alkenyl-, $R^{14}$—C$_{2-6}$alkynyl-, $R^{14}$—C$_{0-6}$alkyloxy-, $R^{14}$—C$_{0-6}$alkylamino- or $R^{14}$—C$_{0-6}$alkyl—S(O)$_r$—; $R^6$ is W—(CR'$_2$)$_q$—Z—(CR'R$^{10}$)—U—(CR'$_2$)$_s$—V— or W'—(CR'$_2$)$_q$—U—(CR'$_2$)$_s$— U and V are absent or CO, CR'$_2$, C(=CR$^{15}_2$), S(O)$_n$, O, NR$^{15}$, CR$^{15'}$OR$^{15}$, CR'(OR")CR'$_2$, CR'$_2$CR'(OR") C(O)CR'$_2$, CR$^{15}_2$C(O), CONR$^{15}$, NR$^{15}$CO, OC(O), C(O)O, C(S)O, OC(S), C(S)NR$^{15}$, NR$^{15}$C(S), SO$_2$NR$^{15}$, NR$^{15}$SO$_2$, N=N, NR$^{15}$NR$^{15}$, NR$^{15}$CR$^{15}_2$, NR$^{15}$CR$^{15}_2$, CR$^{15}_2$O, OCR$^{15}_2$, C$S(m)ZC, CR$^{15}$=CR$^{15}$, Het, or Ar, provided that U and V are not simultaneously absent, and W and W' are a nitrogen-containing substituent, and integrin receptor antagonists.

11 Claims, No Drawings

INTEGRIN RECEPTOR ANTAGONISTS

This application is a 371 of PCT/US96/11108 filed Jun. 28, 1996 which claims the benefit of U.S. Provisional Application 60/000,665 filed Jun. 29, 1995

FIELD OF THE INVENTION

This invention relates to pharmaceutically active compounds which bind to integrins, such as the vitronectin receptor and fibrinogen receptor. Such compounds are useful for inhibiting platelet aggregation and osteoclast attachment to bone.

BACKGROUND OF THE INVENTION

Integrins are a family of heterodimeric proteins which generally mediate cell adhesion. Typical of such proteins are the vitronectin receptor (an $\alpha_v\beta_3$ heterodimer) and the fibrinogen receptor (an $\alpha_{IIb}\beta_3$ heterodimer). The natural ligands of these receptors (e.g., vitronectin and fibrinogen) have been found to share a common -Arg-Gly-Asp- amino acid sequence, which appears to be critical for binding. In fact, many of the integrin receptors appear to cross react with ligands which possess such an amino acid sequence. For instance, the $\alpha_{IIb}\beta_3$ receptor reacts with fibronectin and vitronectin, thrombospondin and von Willebrand factor, as well as fibrinogen. Functionally fibrinogen, a dimer having two binding sites for $\alpha_{IIb}\beta_3$, reacts with activated receptors found on the surface of platelets. The binding of $\alpha_{IIb}\beta_3$ receptors on adjacent platelets, by fibrinogen leads to crosslinking and is considered to be a major factor in platelet aggregation. Compounds which inhibit the binding of the $\alpha_{IIb}\beta_3$ receptor to fibrinogen have been shown to inhibit the platelet aggregation in vitro, and thrombus formation in vivo. See, for instance, EP-A 0 341 915.

The vitronectin receptor is found on a variety of cell types, such as on osteoclasts and the endothelial cells lining blood vessels. Recent studies have indicated that the attachment of osteoclasts to the bone matrix is mediated through these cell surface adhesion receptors. For instance, Davies, et al., *J. Cell Biol.*, 1989, 109, 1817, disclose that the osteoclast functional antigen, which is implicated in the regulation of bone resorption, is biochemically related to the vitronectin receptor. The vitronectin receptor is known to bind to bone matrix proteins, such as osteopontin, bone sialoprotein and thrombospondin, which contain the tripeptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. Bertolini et al., *J. Bone Min. Res.*, 6, Sup. 1, S146, 252 have shown that cylco-S,S-$N^\alpha$-acetyl-cysteinyl-$N^\alpha$-methyl-argininyl-glycyl-aspartyl-penicillamine amide inhibits osteoclast attachment to bone. In addition, Sato, et al.,*J. Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat. EP 528 587 and 528 586 report substituted phenyl derivatives which inhibit osteoclast mediated bone resorption.

Bondinell, et aL, in WO 93/00095 (PCT/US92/05463) and WO 94/14776 (PCT/US93/12436) disclose that certain compounds which have a substituted 6-7 bicyclic ring system are useful for inhibiting the fibrinogen ($\alpha_{IIb}\beta_3$) receptor. Other 6-7 bicyclic ring systems which inhibit the fibrinogen receptor are disclosed by Blackburn et al. in WO 93/08174 (PCT/US92/08788). Blackburn et al., WO 95/04057 (PCT/US94/07989) also disclose compounds which have a five- or six-membered ring fused to such 6-7 bicyclic ring to form a tricyclic ring system, which are useful as antagonists of the fibrinogen receptor. Other compounds having 6-7 bicyclic ring systems that selectively inhibit the vitronectin receptor are disclosed in WO 96/00730 (PCT/US95/08306) and WO 96/00574 (PCT/US95/08146). It has now been discovered that certain new tricyclic ring systems are useful templates for preparing integrin receptor antagonists. It has also been discovered that such a ring system may be used as a template, which may be suitably substituted to prepare compounds which are selective for either the fibrinogen receptor or the vitronectin receptor.

SUMMARY OF THE INVENTION

It is an object of this invention to provide compounds of the formula (I), as described hereinafter, which have pharmacological activity for the inhibition of integrin receptors. It is an object of this invention to provide a template which may be suitably substituted to provide selective binding for specific integrin receptors, especially the fibrinogen ($\alpha_{IIb}\beta_3$) or the vitronectin ($\alpha_v\beta_3$) receptor relative to each other and other integrin receptors.

This invention is also a pharmaceutical composition comprising a compound according to formula (I) and a pharmaceutically carrier.

This invention is also a method of treating diseases in which the pathology may be modified by binding to an integrin receptor, especially the vitronectin or the fibrinogen receptor. In a particular aspect, the compounds of this invention are useful for treating osteoporosis, atherosclerosis, restenosis, cancer and conditions in which it is desirable to inhibit platelet aggregation, such as stroke, transient ischemia attacks, myocardial infarction and rethrombosis following thrombolytic therapy.

DETAILED DESCRIPTION

This invention comprises compounds of formula (I):

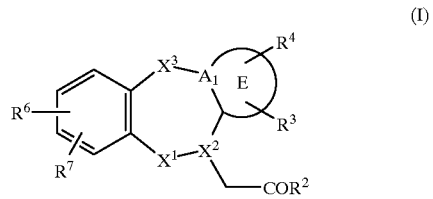

(I)

wherein $A_1$ is C or N;

E is a five- or six-membered heteroaromatic or six-membered aromatic ring optionally substituted by $R^3$ or $R^4$;

$X^1$–$X^2$ is $CHR^1$—CH, $CR^1$=CH, $NR^1$—CH, $S(O)_u$—CH or O—CH;

$X^3$ is $CR^5R^{5'}$, $NR^5$, $S(O)_u$ or O;

R' is H, $C_{1-6}$alkyl, $C_{3-7}$cycloalkyl-$C_{0-4}$alkyl or Ar-$C_{0-4}$alkyl;

R" is R', —C(O)R' or —C(O)OR$^5$;

R'" is $C_{1-6}$alkyl, $C_{3-7}$cycloalkyl-$C_{0-4}$alkyl or Ar-$C_{0-4}$alkyl;

$R^1$ is H, $C_{1-6}$alkyl, $C_{3-7}$cycloalkyl-$C_{0-4}$alkyl or Ar-$C_{0-4}$alkyl;

$R^2$ is —OR', —NR'R", —NR'SO$_2$R'", —NR'OR', —OCR'$_2$C(O)OR', —OCR'$_2$OC(O)_R', —OCR'$_2$C(O)NR'$_2$, CF$_3$ or —COCR'$_2$R$^{2'}$;

$R^{2'}$ is —OR', —CN, —S(O)$_r$R', S(O)$_2$NR'$_2$, —C(O)R' C(O)NR'$_2$ or —CO$_2$R';

$R^5$ and $R^{5'}$ are independently H, C$_{1-6}$alkyl, C$_{3-7}$cycloalkyl-C$_{0-4}$alkyl or Ar-C$_{0-4}$alkyl;

$R^6$ is W—(CR'$_2$)$_q$—Z—(CR'R$^{10}$)$_r$—U—(CR'$_2$)$_s$—V— or W'—(CR'$_2$)$_q$—U—(CR'$_2$)$_s$—;

$R^3$, $R^4$ and $R^7$ are independently H, halo, —OR$^{12}$, —SR$^{12}$, —CN, —NR'R$^{12}$, —NO$_2$, —CF$_3$, CF$_3$S(O)$_r$—, —CO$_2$R', —CONR'$_2$, R$^{14}$—C$_{0-6}$alkyl-, R$^{14}$—C$_{1-6}$oxoalkyl-, R$^{14}$—C$_{2-6}$alkenyl-, R$^{14}$—C$_{2-6}$alkynyl, R$^{14}$—C$_{0-6}$alkyloxy-, R$^{14}$—C$_{0-6}$alkylamino- or R$^{14}$—C$_{0-6}$alkyl-S(O)$_r$—;

$R^8$ is R', C(O)R', CN, NO$_2$, SO$_2$R' or C(O)OR$^5$;

$R^9$ is R', —CF$_3$, —SR', or —OR';

$R^{10}$ is H, C$_{1-4}$alkyl or —NR'R";

$R^{12}$ is R', —C(O)R', —C(O)NR'$_2$, —C(O)OR$^5$, —S(O)$_m$R' or S(O)2NR'$_2$;

$R^{14}$ is H, C$_{3-6}$cycloalkyl, Het or Ar;

$R^{15}$ is H, C$_{1-10}$alkyl, C$_{3-7}$cycloalkyl-C$_{0-8}$alkyl or Ar-C$_{0-8}$alkyl;

U and V are absent or CO, CR'$_2$, C(=CR$^{15}$$_2$), S(O)$_n$, O, NR$^{15}$, CR$^{15'}$OR$^{15}$, CR'(OR")CR'$_2$, CR'$_2$CR'(OR"), C(O)CR'$_2$, CR$^{15}$$_2$C(O), CONR$^{15}$, NR$^{15}$CO, OC(O), C(O)O, C(S)O, OC(S), C(S)NR$^{15}$, NR$^{15}$C(S), SO$_2$NR$^{15}$, NR$^{15}$SO$_2$, NR=N, NR$^{15}$NR$^{15}$, NR$^{15}$CR$^{15}$$_2$, NR$^{15}$CR$^{15}$$_2$, CR$^{15}$$_2$O, OCR$^{15}$$_2$, C≡C, CR$^{15}$=CR$^{15}$, Het, or Ar, provided that U and V are not simultaneously absent;

W is R'R"N—, R'R"NR'N—, R'R"NR'NCO—, R'$_2$NR'NC(=NR')—, R'ONR'C(=NR')—,

R'$_2$N—C(R$^9$)=N—, R'$_2$N—C(R'$_2$N)=N—, R$^9$—C(NR")=NR'—,

R"R'N—C(NR')=Y, R"R'N—C(NR')=N—X—, R"R'N—C(NR$^8$)=NR'—

(N); or W' is R$^a$—pyridyl—, R$^b$,R$^c$-oxazolyl with Q,

R'-oxazolyl with R$^a$, R'-oxazolyl-R$^a$,

R$^b$,R$^c$-imidazolyl with R$^a$, or R$^b$,R$^c$-imidazolyl with R$^a$,

-continued

R$^a$—tetrahydropyrimidinyl with R';

Q is NR',O or S;

$R^a$ is H, C$_{1-6}$alkyl, Ar-C$_{0-6}$alkyl, Het-C$_{0-6}$alkyl, or C$_{3-6}$cycloalkyl-C$_{0-6}$alkyl, halogen, OR$^1$, SR$^1$, COR$^1$, OH, NO$_2$, N(R$^1$)$_2$, CO(NR$^1$)$_2$, CH$_2$N(R$^1$)$_2$;

$R^b$ and $R^c$ are independently selected from H, C$_{1-6}$alkyl, Ar-C$_{0-6}$alkyl, Het-C$_{0-6}$alkyl, or C$_{3-6}$cycloalkyl-C$_{0-6}$alkyl, halogen, OR$^1$, SR$^1$, COR$^1$, OH, NO$_2$, N(R$^1$)$_2$, CO(NR$^1$)$_2$, CH$_2$N(R$^1$)$_2$, or R$_b$ and R$_c$ are joined together to form a five or six membered aromatic or non-aromatic ring, optionally substituted by halogen, C$_{1-4}$alkyl, OR$^1$, SR$^1$, COR$^1$, OH, NO$_2$, N(R$^1$)$_2$, CO(NR$^1$)$_2$, CH$_2$N(R$^1$)$_2$, CN, or R"R'NC(=NR')—;

X is N=CR', C(O) or O;
Y is absent, S or O;
Z is (CH$_2$)$_t$, Het, Ar or C$_{3-7}$cycloalkyl;
m is 1 or 2;
n is 0, 1, 2 or 3;
q is 0, 1, 2 or 3;
r is 0, 1 or 2;
s is 0, 1 or 2;
t is 0, 1 or 2;
u is 0, 1 or 2;
v is 0 or 1; and
w is 0 or 1; or
a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

[structures of keto and enol forms shown]

and tautomers of guanidine-type groups, such as

R"R'N—C(NR')=NR'—X— and R"R'N—C(NR'$_2$)=N—X—, each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

More particularly, the compounds are of the general formula (II) or (III):

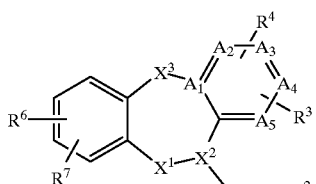
(II)

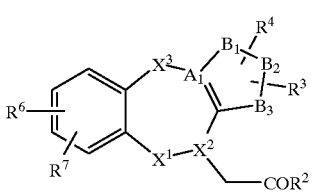
(III)

wherein $A_1$ and $R^1$–$R^{12}$ are as described for formula (I), $A_2$–$A_5$ are chosen from CH, $CR^3$, $CR^4$ and N, and $B_1$–$B_3$ are chosen from $CR^3$, $CR^4$, O, N and S, provided that the resultant E ring is stable and accessible by routine preparative procedures.

In one embodiment, this invention is a carbocyclic compound according to formula (IV):

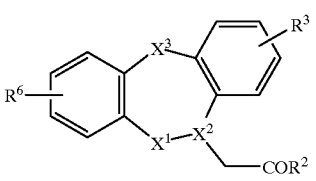
(IV)

In particular, the compound may be of the formulae (V-1) to (V-9):

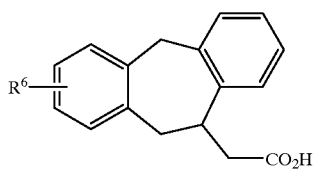
(V-1)

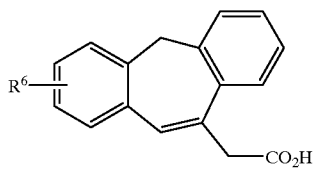
(V-2)

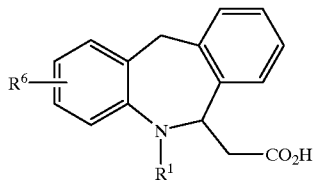
(V-3)

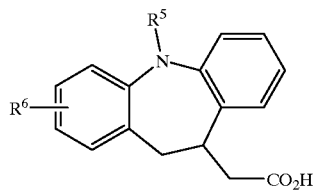
(V-4)

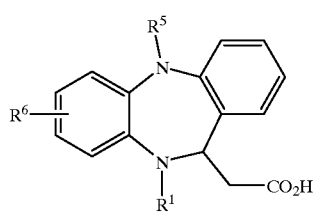
(V-5)

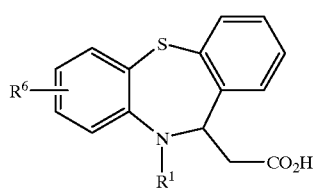
(V-6)

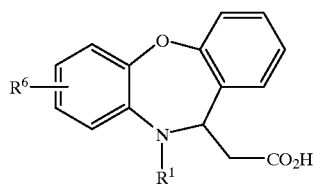
(V-7)

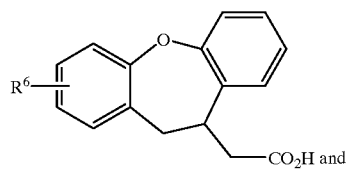
(V-8)

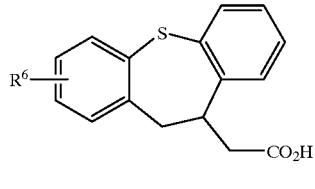
(V-9)

In another embodiment, this invention comprises compounds which are a 6-7 carbocyclic ring system to which a heteroaromatic ring is attached, such as the compounds of formula (VI) or (VII):

(VI)

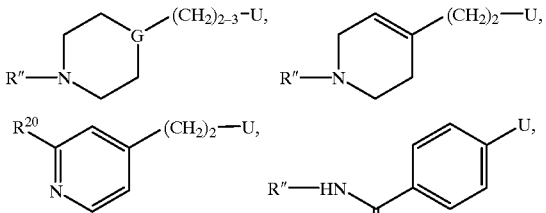

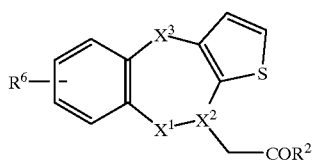
(VII)

In yet another embodiment this invention comprises benzazepine compounds of formula (VIII) or (IX):

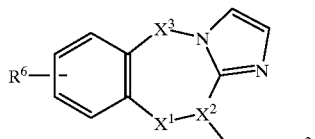
(VIII)

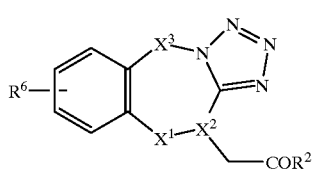
(IX)

Suitably, $A_1$ is C.

Preferably $X^1$-$X^2$ is CHR$^1$—CH or NR$^1$—CH.

Suitably, $X^3$ is CR$^5$R$^{5'}$. Preferably, $X^3$ is CH$_2$.

Suitably R$^1$ is H. Suitably, R$^2$ is OR'. Suitably, R$^3$ and R$^4$ are H.

Suitably, U is CONR$^{15}$, NR$^{15}$CO, CH$_2$CH$_2$, or CH$_2$O, where R$^{15}$ is C$_{1-10}$alkyl, optionally substituted by NO$_2$, CN, CO$_2$R', R$^{14}$—C$_{0-6}$alkyl or R$^{14}$—C$_{0-6}$alkylamino.

Suitably, when U is Ar, it is a phenyl ring, preferably 1,3 disubstituted.

Suitably R$^{15}$ is R'. More suitably R$^{15}$ is C$_{1-6}$alkyl, most suitably H or methyl.

Suitably, when it is desired that compounds of formula (I) should have selective affinity for the fibrinogen receptor, R$^6$ is W—(CR'$_2$)$_q$—Z—(CR'R$^{10}$)$_r$—U—(CR'$_2$)$_s$—V—, and R$^6$ is preferably substituted as:

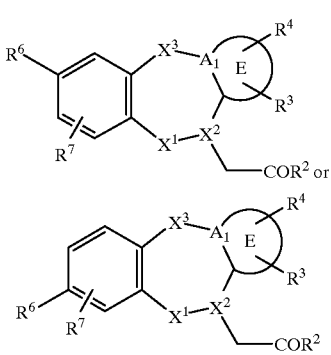

Suitable substituents for R$^6$ when fibrinogen antagonist acitivity is desired are:

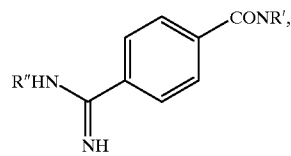

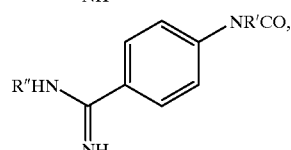

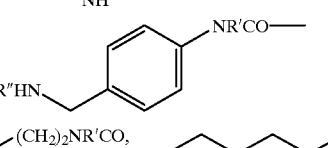

R"HNC(=NH)NH—(CH$_2$)$_3$(CHR$^{10}$)—U, and R"HN—(CH$_2$)$_5$—U wherein G is N or CH, R$^{20}$ is hydrogen, amino, mono or di-C$_{1-4}$alkylamino, hydroxy or C$_{1-4}$alkyl, and U is NR'CO, CONR', (CH$_2$)CO, CH=CH, C≡C, CH$_2$O, OCH$_2$ and (CH$_2$)$_2$.

Particularly good substituents for promoting selective fibrinogen antagonist activity are:

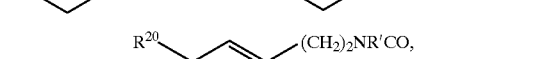

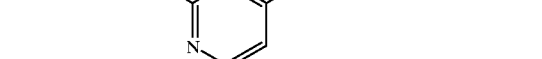

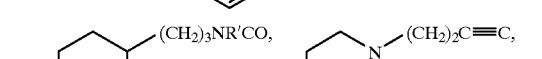

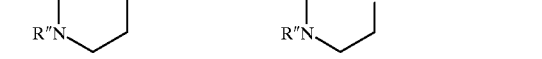

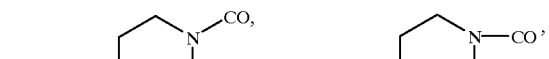

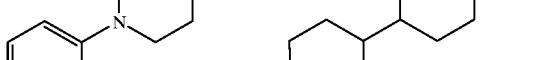

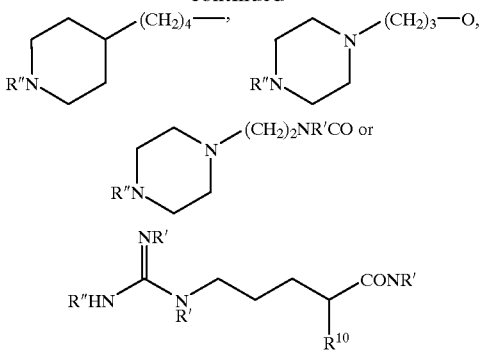

wherein r' are $C_{1-4}$alkyl. Particularly preferred of such groups for $R^6$ are:

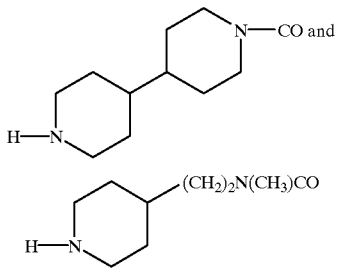

Suitably, when it is desired that compounds of formula (I) should have selective affinity for the vitronectin receptor, $R^6$ is W'—$(CR'_2)_q$—U—, and $R^6$ is preferably substituted

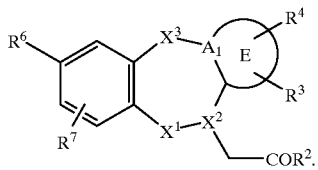

Preferred substituents for W' when vitronectin binding activity is desired are:

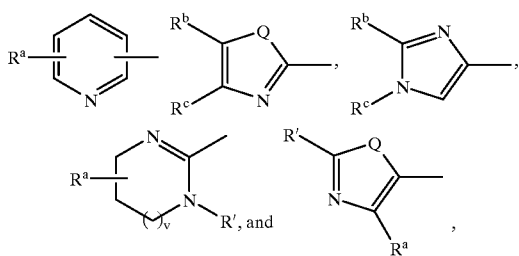

wherein Q is NH. Preferably, $R^b$ and $R^c$ are joined to form a cyclohexyl, phenyl or pyridyl ring. Suitably, $R^a$ is $C_{1-6}$alkyl, $C_{1-6}$alkoxy, halogen or R'NH.

Suitably, —$(CR'_2)_q$—U— is $(CH_2)_q$—NR'CO, $(CH_2)_q$—$CH_2O$ or $(CH_2)_q$—$CH_2CH_2$.

Specific preferred $R^6$ substituents for enhancing vitronectin activity are

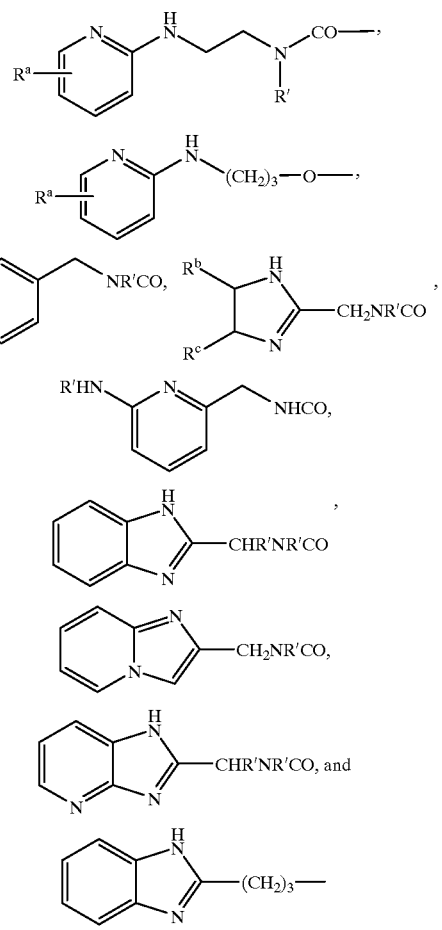

By appropriate selection of the spacing of the substituent W and/or W' from the phenyl ring of the 6-7 ring system, compounds having selective activity for either the vitronectin and fibrinogen receptor, or dual activity for both receptors, may be obtained. In general, fibrinogen antagonist activity will be favored by an intramolecular distance of about 16 angstroms between the oxygen of the carbonyl moiety attached to the seven-membered ring, and the basic nitrogen moiety of W or W'; while vitronectin antagonist activity will be favored by about 14 angstroms between the respective acidic and basic centers.

Specific compounds of this invention are:

(±)-10,11-Dihydro-3-[[[(1H-benzimidazole-2-yl)methyl]amino]carbonyl]-5H-dibenzo[a,d]cycloheptene-10-acetic acid;

(±)-10,11-Dihydro-3-[[[(4-aza-5-methyl-1H-benzimidazole-2-yl)methyl]methylamino]carbonyl]-5H-dibenzo[a,d]cycloheptene-10-acetic acid;

(±)-10,11-Dihydro-3-[[[(1H-benzimidazole-2-yl)methyl]methylamino]carbonyl]-5H-dibenzo[a,d]cycloheptene-10-acetic acid; and (±)-10,11-Dihydro-3-[1-(4,4'-bipiperidinyl)carbonyl]-5H-dibenzo[a,d]cycloheptene-10-acetic acid;

(±)-10,11-Dihydro-3-[3-(2-benzimidazolyl)-1-propyl]-5H-dibenzo[a,d]cycloheptene-10-acetic acid;

(±)-10,11-Dihydro-3-[[[2-(2-pyridylamino)ethyl]amino]carbonyl]-5H-dibenzo[a,d]cycloheptene-10-acetic acid;

(±)-10,11-Dihydro-3-[3-(2-pyridylamino)-1-propyloxy]-5H-dibenzo[a,d]cycloheptene-10-acetic acid; and 2-[[[(1H-Benzimidazol-2-yl)methyl]methylamino]carbonyl]-6,11-dihydro-5H-dibenz[b,e]azepine-6-acetic Acid.

Abbreviations and symbols commonly used in the peptide and chemical arts are used herein to describe the compounds of this invention.

$C_{1-4}$alkyl as applied herein is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. Any $C_{1-4}$alkyl or $C_{1-6}$alkyl group may be optionally substituted by $R^7$ unless otherwise indicated. $C_{0-4}$alkyl and $C_{0-6}$alkyl additionally indicates that no alkyl group need be present (e.g., that a covalent bond is present).

$C_{2-6}$ alkenyl as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included. Any $C_{2-6}$alkenyl group may be optionally substituted by $R^7$ unless otherwise indicated.

$C_{2-6}$ alkynyl means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne. Any sp$^3$ carbon atom in the $C_{2-6}$alkynyl group may be optionally substituted by $R^7$.

$C_{1-4}$oxoalkyl refers to an alkyl group of up to four carbons wherein a $CH_2$ group is replaced by a C(O), or carbonyl, group. Substituted formyl, acetyl, 1-propanal, 2-propanone, 3-propanal, 2-butanone, 3-butanone, 1- and 4-butanal groups are representative. $C_{1-6}$oxoalkyl includes additionally the higher analogues and isomers of five and six carbons substituted by a carbonyl group. $C_{3-6}$oxoalkenyl and $C_{3-6}$oxoalkynyl refers to a $C_{3-6}$alkenyl or $C_{3-6}$alkynyl group wherein a $CH_2$ group is replaced by C(O) group. $C_{3-4}$oxoalkenyl includes 1-oxo-2-propenyl, 3-oxo-1-propenyl, 2-oxo-3-butenyl and the like.

A substituent on a $C_{1-6}$ alkyl, $C_{2-6}$ alkenyl, $C_{2-6}$ alkynyl or $C_{1-6}$ oxoalkyl group, such as $R^7$, may be on any carbon atom which results in a stable structure, and is available by conventional synthetic techniques.

$R^{14}$—$C_{1-6}$ alkyl refers to a $C_{1-6}$ alkyl group wherein in any position a carbon-hydrogen bond is replaced by a carbon-$R^{14}$ bond. $R^{14}$—$C_{2-6}$ alkenyl and $R^{14}$—$C_{2-6}$ alkynyl have a similar meaning with respect to $C_{2-6}$ alkenyl and $C_{2-6}$ alkynyl.

Ar, or aryl, as applied herein, means phenyl or naphthyl, or phenyl or naphthyl substituted by one to three moieties $R^7$. In particular, $R^7$ may be $C_{1-4}$alkyl, $C_{1-4}$alkoxy, $C_{1-4}$alkthio, trifluoroalkyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuran, benzimidazole, benzopyran, benzothiophene, furan, imidazole, indole, indoline, morpholine, piperidine, piperazine, pyrrole, pyrrolidine, tetrahydropyridine, pyridine, thiazole, thiophene, quinoline, isoquinoline, and tetra- and perhydro-quinoline and isoquinoline. A six membered ring heterocycle containing one or two nitrogens, such as piperidine, piperazine, tetrahydropyridine and pyridine, are preferred heterocycles for the moiety Z. Any accessible combination of up to three substituents, such as chosen from $R^7$, on the Het ring that is available by chemical synthesis and is stable is within the scope of this invention.

$C_{3-7}$cycloalkyl refers to an optionally substituted carbocyclic system of three to seven carbon atoms, which may contain up to two unsaturated carbon—carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^7$, on the cycloalkyl ring that is available by conventional chemical synthesis and is stable, is within the scope of this invention.

Ⓝ as used herein indicates a nitrogen heterocycle, which may be a saturated or unsaturated stable five-, six- or seven-membered monocyclic ring, or a seven- to ten-membered bicyclic ring containing up to three nitrogen atoms or containing one nitrogen atom and a heteroatom chosen from oxygen and sulfur, and which may be substituted on any atom that results in a stable structure. The nitrogen atom in such ring may be substituted so as to result in a quaternary nitrogen. The nitrogen heterocycle may be substituted in any stable position by $R^{20}$, for instance H, $C_{1-4}$alkoxy, F, Cl, Br, I, $NO_2$, NR'$_2$, OH, $CO_2$R', CONHR', $CF_3$, $R^{14}$—$C_{0-4}$alkyl, $R^{14}$—$C_{1-4}$alkyl- $S(O)_u$ (e.g., where u is 0, 1 or 2) or $C_{1-4}$alkyl substituted by any of the aforementioned sustituents. Representative of Ⓝ are pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydro- and hexahydro-azepine, quinuclidine, quinuclidinium, quinoline, isoquinoline, and tetra- and perhydro- quinoline and isoquinoline. In particular, Ⓝ may be pyridyl, pyrolidinyl, piperidinyl, piperazinyl, azetidinyl, quinuclidinyl or tetrahydropyridinyl. Ⓝ is preferably 4-pyridyl, 4-(2-amino-pyridyl), 4-tetrahydropyridyl, 4-piperidinyl or 4-piperazinyl.

When $R^b$ and $R^c$ are joined together to form a five- or six-membered aromatic or non-aromatic ring fused to the ring to which $R^b$ and $R^c$ are attached, the ring formed will generally be a five- or six-membered heterocycle selected from those listed above for Het, or will be a phenyl, cyclohexyl or cyclopentyl ring. Benzimidazolyl, 4-azabenzimidazolyl, 5-azabenzimidazolyl and substituted derivatives thereof are preferred moieties for W'.

Certain radical groups are abbreviated herein. t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bn refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. MeArg is Nα-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethylamine, EDC refers to N-ethyl-N' (dimethylaminopropyl)-carbodiimide. HOBt refers to 1-hydroxybenzotriazole, THF refers to tetrahydrofuran, DMF refers to dimethyl formamide, NBS refers to N-bromo-succinimide, Pd/C refers to a palladium on carbon catalyst, DPPA refers to diphenylphosphoryl azide, BOP refers to benzotriazol-1-yloxy-tris(dimethylamino) phosphonium hexafluorophosphate, HF refers to hydrofluoric acid, PPA refers to polyphosphoric acid, TEA refers to triethylamine, TFA refers to trifluoroacetic acid, PCC refers to pyridinium chlorochromate.

A particularly useful intermediate in the preparation of compounds of formula (I) is a compound of formula (X):

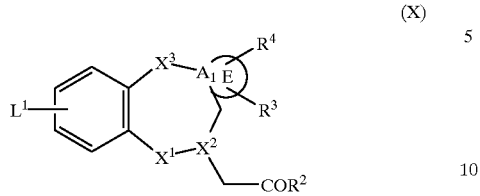

(X)

wherein $X^1$, $X^2$, $X^3$, $R^2$, $R^3$, $R^4$, $A_1$ and E as as defined in formula (I), and $L^1$ is meta to the ring junction and is CHO, $CO_2R'$, Br, I, OH, $CF_3SO_3$, $CH_2$-T or $NR'R^{15}$, and T is OH, $NHR^{15}$, Cl, Br or I. Preferably, $L^1$ is OH, $CF_3SO_3$, $CO_2R'$ or NR'R" and $R^1$ is H, $C_{1-4}$alkyl, $C_{1-4}$oxoalkyl, $R^2$ is $C_{1-6}$alkyl, or benzyl, $R^4$ is H or Q-$C_{1-6}$alkyl, and $R^5/R^{5'}$ are H,H. Preferably $A_1$ and the ring E together form a fused phenyl ring, $X^1$–$X^2$ is $CHR^1$—CH or $NR^1$—CH, and $X_3$ is $CHR^5$.

The compounds of formula (I) are generally prepared by coupling the intermediate of formula (X) with a compound of formula (XI):

(XI)

wherein $R^{6'}$ is W—$(CR'_2)_q$—Z—$(CR'R^{10})_r$—U—$(CR'_2)_s$—$L^2$ or W'—$(CR'_2)_q$—$L^2$, where W, W', R', Z, $R^{10}$, U, q, r and s are as defined in formula (I), and $L^2$ is OH, $NHR^{15}$, C≡C, CHO, $CO_2R'$, Br, I or Cl. In certain cases, it may be desirable to further modify the group W or W' by appropriate reactions to introduce a functional group, or remove a protecting group, as further illustrated herein. The coupling will generally result in the formation of the U or V group, and methods for such coupling reactions are well known in the art. WO 93/08174 (PCT/US92/08788; Genentech), WO 93/08174 (PCT/US92/08788; Genentech), WO 96/00730 (PCT/US95/08306; SmithKline Beecham), WO 96/00574 (PCT/US95/08146; SmithKline Beecham), WO 93/00095 (PCT/US92/05463; SmithKline Beecham) and WO 94/14776 (PCT/US93/12436; SmithKline Beecham) generally disclose such reactions and are incorporated herein by reference.

Compounds of formula X wherein $A^1$ is C and $A^2$–$A^4$ are CH are prepared by the method described in Scheme 1:

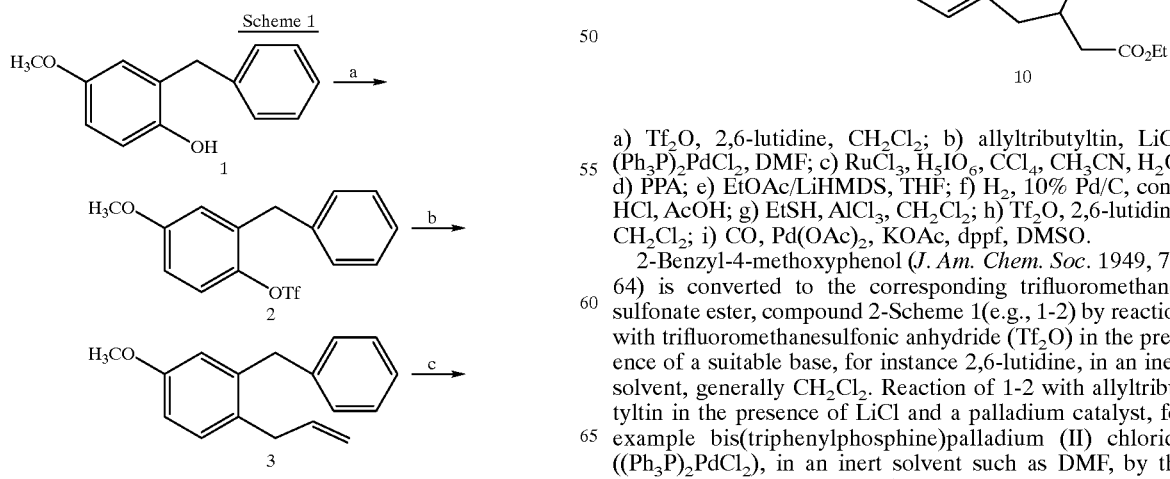

a) $Tf_2O$, 2,6-lutidine, $CH_2Cl_2$; b) allyltributyltin, LiCl, $(Ph_3P)_2PdCl_2$, DMF; c) $RuCl_3$, $H_5IO_6$, $CCl_4$, $CH_3CN$, $H_2O$; d) PPA; e) EtOAc/LiHMDS, THF; f) $H_2$, 10% Pd/C, conc. HCl, AcOH; g) EtSH, $AlCl_3$, $CH_2Cl_2$; h) $Tf_2O$, 2,6-lutidine, $CH_2Cl_2$; i) CO, $Pd(OAc)_2$, KOAc, dppf, DMSO.

2-Benzyl-4-methoxyphenol (*J. Am. Chem. Soc.* 1949, 71, 64) is converted to the corresponding trifluoromethanesulfonate ester, compound 2-Scheme 1(e.g., 1-2) by reaction with trifluoromethanesulfonic anhydride ($Tf_2O$) in the presence of a suitable base, for instance 2,6-lutidine, in an inert solvent, generally $CH_2Cl_2$. Reaction of 1-2 with allyltributyltin in the presence of LiCl and a palladium catalyst, for example bis(triphenylphosphine)palladium (II) chloride (($Ph_3P)_2PdCl_2$), in an inert solvent such as DMF, by the method described by Tilley (*J. Org. Chem.* 1990, 55, 906), affords 1-3. Oxidative cleavage of the olefin in 3-Scheme 1 to afford directly the carboxylic acid 1-4 can be accomplished by reaction with an appropriate oxidizing agent, classically $KMnO_4$, in a suitable aqueous solvent, such as aqueous acetone or aqueous acetic acid. Preferably, however, oxidative cleavage of the olefin in 1-3 to afford directly the carboxylic acid 1-4 is conducted according to the general method of Sharpless (*J. Org. Chem.* 1981, 46, 3936; *J. Org. Chem.* 1985, 50, 1560, footnote 4), wherein $RuO_4$ is generated in situ by the reaction of $RuCl_3$ or $RuO_2$ with $NaIO_4$ or $H_5IO_6$ in a solvent mixture of $CCl_4$, $CH_3CN$, and $H_2O$. Alternatively, the oxidation might be conducted in two operations, involving in the first stage an oxidative cleavage of the olefin to the corresponding aldehyde, which can be accomplished by procedures well known to those of skill in the art, followed by oxidation of the aldehyde to the carboxylic acid using, for example, $NaClO_2$ as described by Pinnick (*Tetrahedron* 1981, 37, 2091) or by Dalcanale and Montanari (*J. Org. Chem.* 1986, 51, 567). Cyclization of 1-4 to 1-5 can be accomplished using polyphosphoric acid, according to the method described by Proctor, Renfrew, and Savage (*J. Chem. Soc. (C)* 1969, 1000). Alternatively, 1-4 can be converted to 1-5 via the corresponding acid chloride of 1-4, which can be prepared by methods well-known to those of skill in the art. Treatment of this acid chloride with an appropriate Friedel-Crafts catalyst, such as $AlCl_3$ or $SnCl_4$, in an inert solvent, such as $CH_2Cl_2$ or $CS_2$, provides the cyclic ketone 1-5. Reaction of 1-5 in an aldol-type reaction with the enolate of ethyl acetate, which can be generated from ethyl acetate on exposure to an appropriate amide base, for instance lithium diisopropylamide (LDA) or lithium bis(trimethylsilyl)amide (LiHMDS), gives 1-6. Frequently, THF is the solvent of choice for an aldol reaction, although THF in the presence of various additives, for instance HMPA or TMEDA, is often used. Reduction of 1-6 to give 1-7 can be accomplished by hydrogenolysis over an appropriate catalyst, for example palladium metal on activated carbon (Pd/C), in an appropriate solvent, such as acetic acid, in the presence of a mineral acid such as HCl. Alternatively, this reduction can be accomplished by treatment of 1-6 with triethylsilane in the presence of boron trifluoride etherate by the general method of Orphanopoulos and Smonu (*Synth. Commun.* 1988, 833). Removal of the methyl ether of 1-7 to give 1-8 can be accomplished with $BBr_3$ in an inert solvent, for example $CH_2Cl_2$, of by reaction with ethanethiol and $AlCl_3$ in an inert solvent, preferably $CH_2Cl_2$. Other useful methods for removal of a methyl ether are described in Greene, "Protective Groups in Organic Synthesis" (published by John Wiley and Sons). 1-9, the trifluoromethanesulfonate ester of 1-8, prepared by the method described earlier for the conversion of 1-1 to 1-2, reacts with carbon monoxide in the presence of potassium acetate, 1,1'-bis(diphenylphosphino)ferrocene (dppf), and a palladium catalyst, for instance palladium acetate $(Pd(OAc)_2)$, in a suitable solvent, preferably DMSO, according to the general method described by Cacchi and Lupi (*Tet. Lett.* 1992, 33, 3939), to give 1-10.

It will be apparent from the above description that if one dehydrates compound 1-6 instead of performing a hydrogenation, one obtains compounds of the general formula (V-2).

Compounds of formula (I) wherein $X^3$ is $NR^5$, O or $S(O)_{0-2}$ are prepared using the general method of Scheme 1, except, for example, by substituting compound 1-4 with a 4-methoxy-2-(phenylamino)-, 2-(phenyloxy)-, or 2-(phenylthio)-phenylacetic acid that may be prepared by methods known to the art.

Compounds of formula (X) wherein $X^1$–$X^2$ is $NR^1$—CH and X3 is $CR^5CR^5$, NR', O or $S(O)_{0-2}$ are prepared using the general method described in Scheme 2:

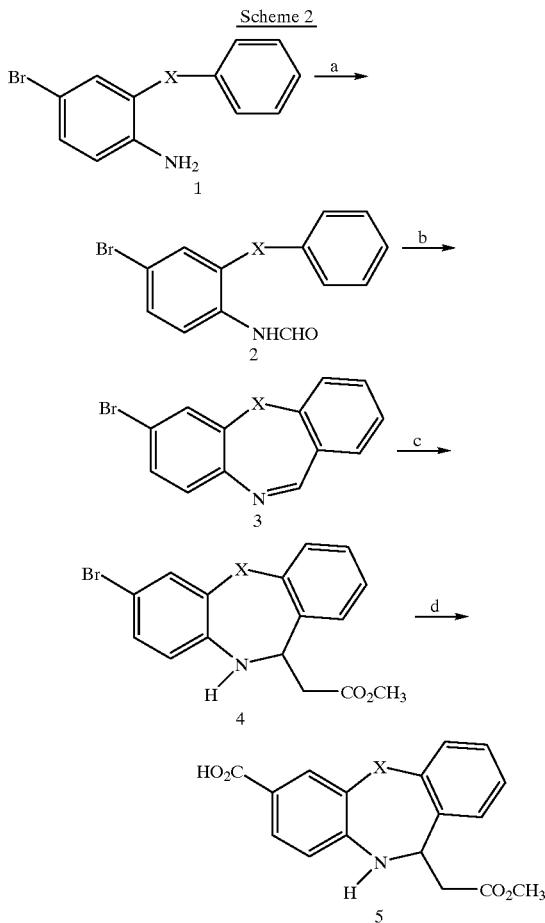

a) $HCO_2H$, $Ac_2O$, $\Delta$; b) $POCl_3$, PPA, $\Delta$; c) $CH_2$=$C(OCH_3)$ $Si(CH_3)_2$-t-Bu, TMSCN, [Rh(COD)Cl]$_2$, $CH_2Cl_2$; d) CO, $Pd(OAc)_2$, KOAc, dppf, DMSO.

Compounds 1-Scheme 2 (e.g., 2-1), are synthesized by methods known to the art. Alternatively, the bromo can be replaced by iodo, trifluoromethanesulfonyloxy or a group that can be converted to bromo, iodo or trifluoromethanesufonyloxy. Compounds 2-1 are converted to the N-formyl compounds 2-2 by treatment with a suitable reagent such as formic acid, an ester of formic acid, or acetic-formic anhydride in a suitable solvent at a suitable temperature. Compounds 2-2 are converted to the cyclic imines 2-3 by treatment with a suitable agent such as a mixture of polyphosphoric acid and phosphoryl chloride at a suitable temperature. Compounds 2-3 are converted to the acetates 2-4 by treatment with a suitable reagent such as the t-butyldimethylsilyl ketal acetal of methyl acetate in the presence of trimethylsilyl cyanide and a suitable catalyst such as di-μ-chloro-bis(1,5-cyclooctadiene)-dirhodium ([Rh (COD)Cl]2) in a suitable solvent such as dichloromethane using the general procedure in *Bull. Chem. Soc Jpn.* 1990, 63, 3122–3131. Alternatively, a Reformatsky reagent may be employed using the general procedure in *Bull. Soc. Chim. Fr.* 1973, 1668. Alternatively, acetic anhydride in acetic acid may be employed using the general procedure in *J. Am. Chem. Soc.* 1950, 72, 3874.

Compounds 2-4 are converted to the carboxylic acids 2-5 according to the general method described in Scheme 1.

Compounds of formula I where U is NR'CO may also be accessed directly from compounds 1-9 or 2-5 by treatment with CO, a primary or secondary amine and a palladium catalyst using the general method of *J. Org. Chem.* 1974, 39, 3327.

The simple tri-substituted benzene starting materials are commercially available or prepared by routine methods well known in the art.

Coupling methods to form amide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference. Coupling reagents as used herein denote reagents which may be used to form amide bonds. Typical coupling methods employ carbodiimides, activated anhydrides and esters and acyl halides. Reagents such as EDC, DCC, DPPA, BOP reagent, HOBt, N-hydroxysuccinimide and oxalyl chloride are typical.

Typically, the amine or aniine is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds such as 1-10 are converted to compounds of formula (I) by a coupling reaction, such as an amide coupling reaction as in Scheme 3.

Scheme 3

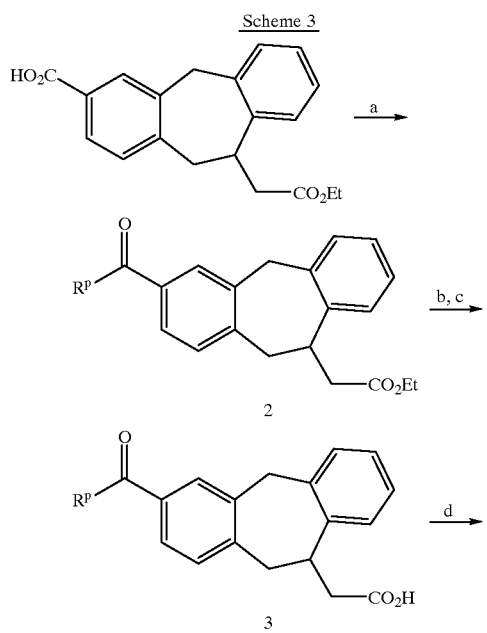

a) 1-BOC-4,4'-bipiperidine [RP], EDC, HOBt.H$_2$O, (i-Pr)$_2$NEt, DMF; b) 1.0 N LiOH, THF, H$_2$O; c) 1.0 N HCl, H$_2$O; d) TFA, CH$_2$Cl$_2$ [R=1-(4,4'-bipiperidine)].

Ethyl ($\pm$)-10,11-dihydro-3-carboxy-5H-dibenzo[a,d] cycloheptene-10-acetate (1-10), prepared as described in Scheme 1, is converted to an activated form of the carboxylic acid using, for example, EDC and HOBt, or SOCl$_2$, and the activated form is subsequently reacted with an appropriate amine, for instance 1-BOC-4,4'-bipiperidine or 2-(methylamino)methylbenzimidazole dihydrochloride, in a suitable solvent such as DMF, CH$_2$Cl$_2$, or CH$_3$CN, to afford compound 2-Scheme 3 (e.g., 3-2). Depending on whether acid neutralization is required, an added base, such as diisopropylethylamine ((i-Pr)$_2$NEt) or pyridine, may be used. Many additional methods for converting a carboxylic acid to an amide are known, and can be found in standard reference books, such as "Compendium of Organic Synthetic Methods", Vol. I–VI (published by Wiley-Interscience). The ethyl ester 5-2 is hydrolyzed using aqueous base, for example, LiOH in aqueous THF or NaOH in aqueous methanol, and the intermediate carboxylate salt is acidified with a suitable acid, for instance TFA or HCl, to afford the carboxylic acid 1-3. Alternatively, the intermediate carboxylate salt can be isolated, if desired, or a carboxylate salt of the free carboxylic acid can be prepared by methods well-known to those of skill in the art. If the amine component of the amide bond-forming reaction (1-10 to 3-2) contains a protecting group, the protecting group can be removed either prior or subsequent to the ester hydrolysis step, using methods suitable for selective deprotection of the specific protecting group employed. Such methods are described in Green, "Protective Groups in Organic Synthesis" (published by Wiley-Interscience). For example, if the amine component contains a nitrogen group which is protected by a tert-butoxycarbonyl (BOC) group, such as in compound 3-3, the BOC group is removed under acidic conditions, using, for instance, 4 N HCl in dioxane or trifluoroacetic acid (TFA) in CH$_2$Cl$_2$, to give the ammonium salt of 3-4. The ammonium salt can be neutralized, if desired, by methods known to those of skill in the art.

Scheme 4 is illustrative of a carbon-carbon bond-forming coupling method which may be used to introduce a carbon-carbon triple bond, double bond or single bond by the opotional application of an appropriate reducing agent (e.g., in step b).

Scheme 4

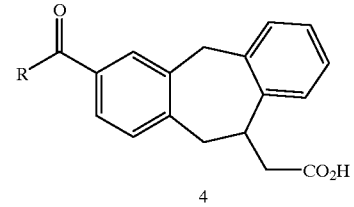

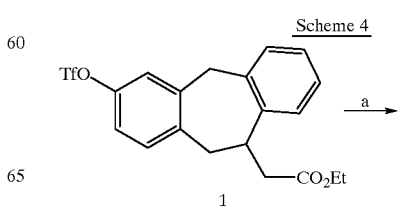

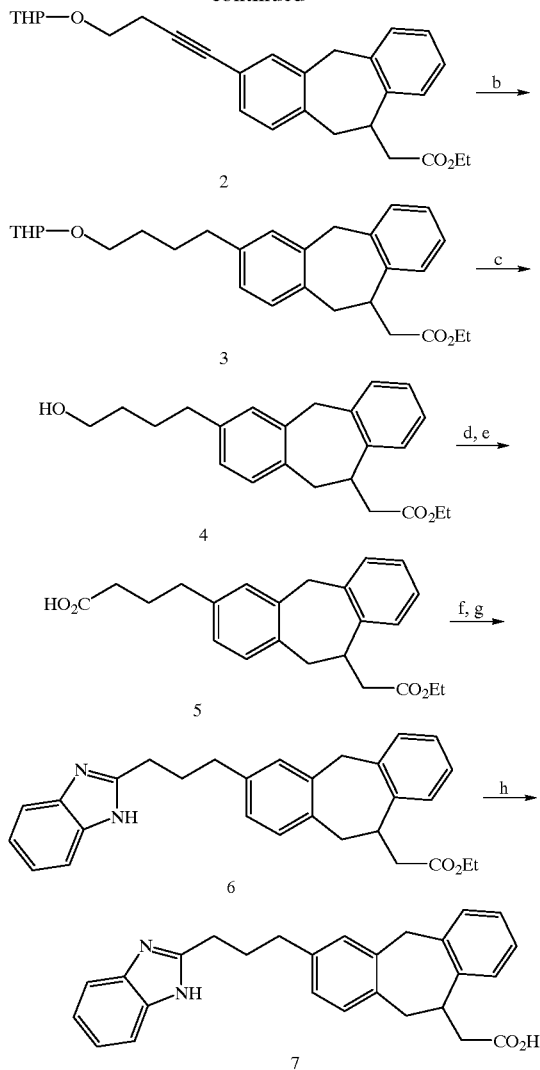

phenylenediamine; g) AcOH, THF; h) 1.0 N NaOH, EtOH, then acidification.

Compound 1-Scheme 4 (4-1), is reacted with 4-(2-tetrahydropyranyloxy)-1-tributylstannyl-1-butyne in a Stille-type coupling reaction of aromatic triflates and organostannanes (*J. Am. Chem. Soc.* 1987, 109, 5478–5486) to afford 4-2. The reaction is catalyzed by a palladium salt, preferably bis(triphenylphosphine)palladium (II) chloride ((PPh$_3$)$_2$PdCl$_2$), and is conducted in the presence of lithium chloride, in an appropriate inert solvent, generally DMF or 1,4-dioxane. Reduction of the acetylenic unit of 4-2 is accomplished under standard hydrogenation conditions which are well-known to those of skill in the art. The resulting compound, 4-3, is deprotected under standard conditions for removal of a tetrahydropyranyl (THP) ether, to afford 4-4. A variety of conditions for deprotection of THP ethers are described in standard reference volumes, such as Greene, "Protective Groups in Organic Synthesis" (published by Wiley-Interscience). The primary alcohol moiety of 4-4 is oxidized to the corresponding carboxylic acid 4-5 by the two-step method described by Wovkulich (*J. Org. Chem.* 1993, 58, 832–839). Many alternative methods for the oxidation of a primary alcohol to the corresponding carboxylic acid have been described, and can be found in such reference volumes. Conversion of the carboxylic acid of 4-5 to the benzimidazole derivative 4-6 follows the general procedures described in WO. Thus, 4-5 is initially converted to an activated form of the carboxylic acid using, for example, isobutyl chloroformate, in the presence of a suitable base, generally 4-methylmorpholine, triethylamine, or diisopropylethylamine, in an inert solvent such as THF or CH$_2$Cl$_2$. The activated form is subsequently reacted with an excess of an appropriate 1,2-diaminoaromatic derivative, for instance 1,2-phenylenediamine, to afford the corresponding mono-amide. The mono-amide is then cyclized under standard conditions, for instance acetic acid in refluxing THF, to afford 4-6. The ethyl ester of 4-6 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid 4-7. Alternatively, the intermediate carboxylate salt can be isolated, if desired, or a carboxylate salt of the free carboxylic acid can be prepared by methods well-known to those of skill in the art.

Scheme 5 is illustrative of a carbon—oxygen bond forming coupling method that may be used to form an ether linkage. Similar coupling methods may also be used to form sulfide and amine linkages.

THPOCH$_2$CH$_2$CCSn(Bu)$_3$, (PPh$_3$)$_2$PdCl$_2$, LiCl, dioxane; b) H$_2$, 10% Pd/C, EtOAc; c) p-TsOH.H$_2$O, EtOH; d) 2,2,6,6-tetramethyloxopiperidinium chloride, CH$_2$Cl$_2$; e) NaClO$_2$, Na$_2$HPO$_3$, 2-methyl-2-butene, H$_2$O; f) isobutyl chloroformate, 4-methylmorpholine, then 1,2-

Scheme 5

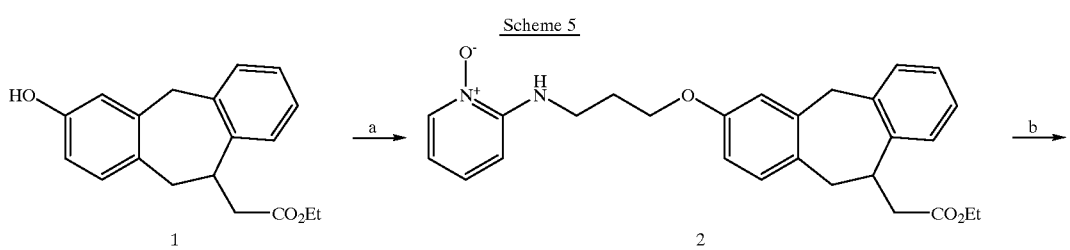

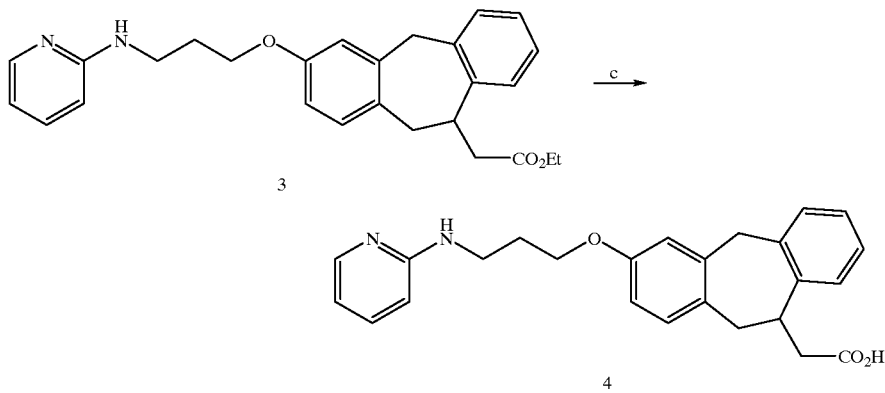

a) 2-[(3-hydroxy-1-propyl)amino]pyridine-N-oxide, DEAD, (Ph)$_3$P, DMF; b) cyclohexene, 10% Pd/C, 2-propanol; c) 1.0 N NaOH, EtOH, then acidification.

Compound 1 of Scheme 5 (5-1) is reacted with 2-[(3-hydroxy-1-propyl)amino]pyridine-N-oxide in a Mitsunobu-type coupling reaction (*Organic Reactions* 1992, 42, 335–656; *Synthesis* 1981, 1–28) to afford 5-2. The reaction is mediated by the complex formed between diethyl azodicarboxylate and triphenylphosphine, and is conducted in an aprotic solvent, for instance THF, CH$_2$Cl$_2$, or DMF. The pyridine-N-oxide moiety of 5-2 is reduced to the corresponding pyridine 5-3 under transfer hydrogenation conditions using a palladium catalyst, preferably palladium metal on activated carbon, in an inert solvent, for instance methanol, ethanol, or 2-propanol. Cyclohexene, 1,4-cyclohexadiene, formic acid, and salts of formic acid, such as potassium formate or ammonium formate, are commonly used as the hydrogen transfer reagent in this type of reaction. The ethyl ester of 5-3 is saponified as described in Scheme 1 to afford 5-4.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li$^+$, Na$^+$, K$^+$, Ca$^{++}$, Mg$^{++}$ and NH$_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein which are antagonists of the vitronectin receptor, are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, antiinflammatory, anti-angiogenic and anti-metastatic agents, and be useful in the treatment of cancer, atherosclerosis and restenosis. In particular, the compounds of this invention are useful for inhibiting restenosis following angioplasty.

The compounds of this invention which inhibit fibrinogen binding provide a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

This invention further provides a method for inhibiting the reocclusion of an artery or vein following fibrinolytic therapy, which comprises internal administration of a compound of formula (I) and a fibrinolytic agent. Administration of a compound of formula (I) in fibrinolytic therapy either prevents reocclusion completely or prolongs the time to reocclusion. When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof.

The compounds of this invention may also be used in vitro to inhibit the aggregation of platelets in blood and blood products, e.g., for storage, or for ex vivo manipulations such as in diagnostic or research use.

The compound is administered either orally or parenterally to the patient, in a manner such that the concentration of drug is sufficient to inhibit bone resorption, or inhibit platelet aggregation or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

The compounds may be tested in one of several biological assays to determine the concentration of compound which is required to have a given pharmacological effect.

INHIBITION OF VITRONECTIN BINDING

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 μg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 μM. This solution is then diluted to the required final compound concentration. Various concentrations of unlabeled antagonists (0.001–100 μM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 μM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i = IC_{50}/(1+L/K_d)$, where L and $K_d$ were the concentration and the dissociation constant of [$^3$H]-SK&F-107260, respectively.

Compounds of the present invention inhibit vitronectin binding to SK&F 107260 in the concentration range of 0.1 to 25 micromolar. Preferred compounds inhibit vitronectin binding at a concentration of less than 1 micromolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

PARATHYROIDECTOMIZED RAT MODEL

Each experimental group consists of 5–6 male Sprague-Dawley rats. The rats are parathyroidectomized (by the vendor, Taconic Farms) 7 days prior to use. Twenty four hours prior to use, circulating ionized calcium levels are measured in whole blood immediately after it has been withdrawn by tail venipuncture into heparinized tubes. Rats are included if ionized Ca level (measured with a Ciba-Coming model 634 calcium pH analyzer) is ≦1.2 mM/L. The rats are then put on a diet of calcium-free chow and deionized water. At the start of the experiment the rats weigh approximately 100 g. Baseline Ca levels are measured and the rats are administered control vehicle (saline) or compound (dissolved in saline) as a single intravenous (tail vein) bolus injection followed immediately by a single subcutaneous injection of either human parathyroid hormone 1-34 peptide (hPTH1-34, dose 0.2 mg/kg in saline/0.1% bovine serum albumen, Bachem, Calif.) or the PTH vehicle. The calcemic response to PTH (and any effect of compound on this response) is measured 2 h after compound/PTH administration.

RAT ULNA DRIFT MODEL

Each experimental group consists of 8–10 male Sprague-Dawley or Wistar rats of approximately 30–40 g body weight at the start of the experiment. The agent being tested is administered by an appropriate route as single or multiple daily doses for a period of seven days. Prior to administration of the first dose, the rats are given a single dose of a fluorescent marker (tetracycline 25 mg/kg, or calcein 10 mg/kg) that labels the position of bone forming surfaces at that point in time. After dosing of compound has been completed, the rats are killed and both forelimbs are removed at the elbow, the foot is removed at the ankle and the skin removed. The sample is frozen and mounted vertically on a microtome chuck. Cross sections of the midshaft region of the ulna are cut in the cryostat. The rate of bone resorption is measured morphometrically in the medial-dorsal portion of the cortical bone. The measurement is done as follows: the amount of bone resorbed at the periosteal surface is equal to the distance by which the periosteal surface has advanced towards the fluorescent label which had been incorporated at the endosteal bone formation surface on day zero; this distance is calculated by subtracting the width of bone between the label and the periosteal surface on day 7 from the width on day zero; the resorption rate in microns per day is calculated by dividing the result by 7.

HUMAN OSTEOCLAST RESORPTION ASSAY ("PIT ASSAY")

Aliquots of osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

Aspirate the medium and replace it with murine anti-HLA-DR antibody, diluted 1:3 in RPMI-1640 medium. Incubate for 30 mins on ice and mix the cell suspension frequently.

The cells are washed ×2 with cold RPMI-1640 by centrifugation (1000 rpm, 5 mins at 40° C.) and the cells are transferred to a sterile 15 ml centrifuge tube. The number of mononuclear cells are enumerated in an improved Neubauer counting chamber.

Sufficient magnetic beads (5/mononuclear cell), coated with goat anti-mouse IgG, are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The osteoclasts are enumerated in a counting chamber, using a large-bore disposable plastic pasteur to charge the chamber with the sample.

The cells are pelleted by centrifugation and the density of osteoclasts adjusted to $1.5 \times 10^4$/ml in EMEM medium, supplemented with 10% fetal calf serum and 1.7 g/litre of sodium bicarbonate.

3 ml aliquots of the cell suspension (per treatment) are decanted into 15 ml centrifuge tubes. The cells are pelleted by centrifugation.

To each tube 3 ml of the appropriate treatment are added (diluted to 50 uM in the EMEM medium). Also included are appropriate vehicle controls, a positive control (87MEM1 diluted to 100 ug/ml) and an isotype control (IgG2a diluted to 100 ug/ml). Incubate at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh treatment or control. Incubate at 37° C. for 48 hours. tartrate resistant acid phosphatase (trap) procedure (selective stain for cells of the osteoclast lineage).

The slices are washed in phosphate buffered saline and fixed in 2% gluteraldehyde (in 0.2M sodium cacodylate) for 5 mins.

They are washed in water and incubated in TRAP buffer for 5 mins at 37° C.

Following a wash in cold water they are incubated in cold acetate buffer/fast red garnet for 5 mins at 4° C.

Excess buffer is aspirated, and the slices are air dried following a wash in water.

The TRAP positive osteoclasts are enumerated by brightfield microscopy and are then removed from the surface of the dentine by sonication.

Pit volumes are determined using the Nikon/Lasertec ILM21W confocal microscope.

INHIBITION OF RGD-MEDLATED $\alpha_{IIb}\beta_3$ BINDING

Purification of $\alpha_{IIb}\beta_3$

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained $\alpha_{IIb}\beta_3$ was eluted with buffer A containing 10% dextrose. All procedures were performed at 4° C. The $\alpha_{IIb}\beta_3$ obtained was >95% pure as shown by SDS polyacrylamide gel electrophoresis.

Incorporation of $\alpha_{IIb}\beta_3$ in Liposomes

A mixture of phosphatidylserine (70%) and phosphatidylcholine (30%) (Avanti Polar Lipids) were dried to the walls of a glass tube under a stream of nitrogen. Purified $\alpha_{IIb}\beta_3$ was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The $\alpha_{IIb}\beta_3$-containing liposomes wee centrifuged at 12,000 g for 15 min and resuspended in the dialysis buffer at a final protein concentration of approximately 1 mg/mL. The liposomes were stored at −70° C. until needed.

Competitive Binding to $\alpha_{IIb}\beta_3$

The binding to the fibrinogen receptor ($\alpha_{IIb}\beta_3$) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 μg of the purified platelet $α_{IIb}β_3$-containing liposomes. The mixtures were incubated for 1 h at room temperature. The $α_{IIb}β_3$-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis.

Inhibition of platelet aggregation may be measured by the method described in WO 93/00095 (PCT/US/92/05463). In vivo thrombus formation is demonstrated by recording the systemic and hemodynamic effects of infusion of the peptides into anesthetized dogs according to the methods described in Aiken et al., *Prostaglandins*, 19, 620 (1980).

Preferred compounds of this invention have an affinity for the vitronectin receptor relative to the fibrinogen receptor, or for the fibrinogen receptor relative to the vitronectin receptor, of greater than 5:1. More preferred compounds have a ratio of activity of greater than 10:1. The most preferred compounds have a selectivity of greater than 100:1. The comparative results of the enhanced binding of the compounds of this invention to the vitronecton receptor relative to the fibrinogen receptor are given in Table 1 below:

| Compound (Ex. #) | Ki/$α_{IIb}β_3$ (uM) | Ki/$α_Vβ_3$ (uM) |
| --- | --- | --- |
| 1 | >50 | 0.023 |
| 2 | 0.009 | 15 |

Vascular Smooth Muscle Cell Migration Assay

The compounds of the instant invention were tested for their ability to inhibit the migration and proliferation of smooth muscle tissue in an artery or vein in order to assess their ability to prevent restenosis of an artery, such as that which typically occurs following angioplasty.

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of 2.5–5.0×10$^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

GENERAL

Nuclear magnetic resonance spectra were recorded at either 250 or 400 MHz using, respectively, a Bruker AM 250 or Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers (cm$^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5 μ Apex-ODS indicates an octadecylsilyl derivatized silica gel chromatographic support having a nominal particle size of 5 μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

PREPERATION 1

Preparation of ethyl (±)-10,11-dihydro-3-carboxy-5H-dibenzo[a,d]cycloheptene-10-acetate a) 3-Benzyl4-(trifluoromethanesulfonyloxy)anisole Trifluoromethanesulfonic anhydride (10.0 mL, 60 mmol) was added over 3 min to a solution of 2-benzyl-4-methoxyphenol (10.71 g, 50 mmol; prepared according to *J. Am. Chem. Soc.* 1949, 71, 64) and anhydrous 2,6-lutidine (12.0 mL, 100 mmol) in anhydrous $CH_2Cl_2$ (250 mL) at −78° C. under argon. The reaction was stirred at −78° C. for 0.5 h, then was warmed to RT. After 1 h, the reaction was diluted with hexanes (250 mL) and washed sequentially with 1.0 N HCl (2×100 mL), 1.0 N NaOH (2×50 mL), H$_2$O (100 mL) and brine (50 mL). Drying (Na$_2$SO$_4$), concentration, and silica gel chromatography (10% EtOAc/hexanes) gave the title compound as a light yellow solid (16.65 g, 96%): TLC R$_f$ 0.51 (10% EtOAc/hexanes); $^1$H NMR (250 MHz, CDCl$_3$) δ 7.10–7.40 (m, 6H), 6.77 (dd, J=9.0, 3.1 Hz, 1H), 6.66 (d, J=3.1Hz, 1H), 4.03 (s, 2H), 3.73 (s, 3H); FTIR (CCl$_4$) 1492, 1423, 1405, 1249, 1216, 1161, 1144, 1039, 869 cm$^{-1}$; MS (ES) m/e 369 (M+Na)$^+$, 364.0 (M+NH$_4$)$^+$, 347.0 (M+H)$^+$.

b) 4-Allyl-3-benzylanisole

LiCl (3.08 g, 72.8 mmol) in a roundbottom flask was flame-dried in high vacuum, and the system was allowed to cool to RT under argon. 3-Benzyl-4-(trifluoromethanesulfonyloxy)anisole (21.0 g, 60.6 mmol), bis(triphenylphosphine)palladium(II) chloride (2.13 g, 3.0 mmol), anhydrous DMF (150 mL), and allyltributyltin (22.6 mL, 72.8 mmol) were added, and the mixture was purged with argon through three evacuation/argon flush cycles. The mixture was heated in an oil bath preset at 95° C., affording a yellow, homogeneous solution. After 1.5 h, the dark mixture was concentrated on the rotavap (high vacuum), and the residue was reconcentrated from xylenes. The resulting residue was taken up in Et$_2$O (120 mL) and stirred briskly with 10% KF (120 mL) for 0.5 h. The layers were separated, and the aqueous layer was extracted with Et$_2$O (2×120 mL). The combined organics were filtered through celite® to remove the insoluble solids, and the filtrate was washed sequentially with H$_2$O (60 mL) and brine (60 mL). Drying (MgSO$_4$) and concentration left a cloudy, yellow oil. Chromatography (silica gel, 5% EtOAc/hexanes) gave the title compound as a light yellow oil (14.21 g, 98%): TLC R$_f$ (5% EtOAc/hexanes) 0.51; $^1$H NMR (250 MHz, CDCl$_3$) δ 7.03–7.31 (m, 6H), 6.74 (dd, J=8.3, 2.7 Hz, 1H), 6.66 (d, J=2.7 Hz, 1H), 5.79–5.98 (m, 1H), 4.89–5.07 (m, 2H), 3.97 (s, 2H), 3.75 (s, 3H), 3.21–3.33 (m, 2H); FTIR (CCl$_4$) 1610, 1496, 1256, 1046, 914 cm$^{-1}$; MS (ES) m/e 239.2 (M+H)$^+$.

c) 2-Benzyl-4-methoxyphenylacetic acid

A solution of H$_5$IO$_6$ (23.83 g, 104.5 mmol) in H$_2$O (56 mL) was added to a solution of 4-allyl-3-benzylanisole (5.30 g, 22.24 mmol) in CCl$_4$ (28 mL) and CH$_3$CN (28 mL), and the well-stirred mixture was cooled thoroughly to 0° C. RuCl$_3$ (231 mg, 1.11 mmol) was added, and the reaction was stirred briskly at 0° C. for 4 h, then at RT for 45 min. The mixture was filtered through celite®, and the filter pad was washed with CH$_2$Cl$_2$ (120 mL) then with H$_2$O (120 mL). The layers were separated and the aqueous layer was extracted with CH$_2$Cl$_2$ (3×120 mL). Drying (Na$_2$SO$_4$) and concentration left a brown oil. This was partitioned between Et$_2$O (90 mL) and 0.25 N NaOH (90 mL), and the layers were separated. The Et$_2$O layer was extracted with 0.25 N NaOH (2×10 mL), and the combined aqueous layers were acidified (pH 2) with conc. HCl. CH$_2$Cl$_2$ extraction, drying (Na$_2$SO$_4$), and concentration gave the title compound as a yellow oil which solidified to a yellow solid (4.19 g, 74%): $^1$H NMR (250 MHz, CDCl$_3$) δ 7.05–7.35 (m, 6H), 6.77 (dd, J=8.3, 2.7 Hz, 1H), 6.71 (d, J=2.7 Hz, 1H), 4.00 (s, 2H), 3.76 (s, 3H), 3.54 (s, 2H); FTIR (CCl$_4$) 2300–3500 (broad), 1710, 1611, 1502, 1496, 1285, 1257, 1045 cm$^{-1}$; MS (ES) m/e 279.0 (M+Na)$^+$, 274.0 (M+NH$_4$)$^+$, 257.0 (M+H)$^+$.

d) 3-Methoxy-5H-dibenzo[a,d]cycloheptene-10(11H)-one

Finely powdered 2-benzyl-4-methoxyphenylacetic acid (3.26 g, 12.72 mmol) was added to well-stirred polyphosphoric acid (165 g) at 100–110° C. After 15 min, the reaction was poured onto ice (330 g). Et$_2$O (330 mL) was added, and the mixture was stirred briskly for 15 min. The layers were separated, and the aqueous layer was extracted with Et$_2$O (330 mL). The combined organic layers were washed with 5% NaHCO$_3$ (2×80 mL) then with brine (80 mL), dried (MgSO$_4$), and concentrated. The residue was reconcentrated from toluene, then was chromatographed (silica gel, 20% EtOAc/hexanes). The title compound was obtained as a yellow solid (1.44 g, 48%): TLC R$_f$ (20% EtOAc/hexanes) 0.46; $^1$H NMR (250 MHz, CDCl$_3$) δ 8.07–8.15 (m, 1H), 7.39–7.49 (m, 1H), 7.25–7.48 (m, 2H), 7.19 (d, J=8.3 Hz, 1H), 6.86 (d, J=2.6 Hz, 1H), 6.71 (dd, J=8.3, 2.6 Hz, 1H), 4.21 (s, 2H), 4.11 (s, 2H), 3.77 (s, 3H); FTIR (CCl$_4$) 1680, 1501, 1282, 1270 cm$^{-1}$; MS (ES) m/e 261 (M+Na)$^+$, 256.0 (M+NH$_4$)$^+$, 239.0 (M+H)$^+$.

e) Ethyl (±)-10,11-dihydro-10-hydroxy-3-methoxy-5H-dibenzo[a,d]cycloheptene-10-acetate Anhydrous EtOAc (0.58 mL, 6.6 mmol) was added dropwise to a solution of lithium bis(trimethylsilyl)amide (1.0 M in THF, 6 mL, 6 mmol) in dry THF (24 mL) in a flame-dried flask at −78° C. under argon. The yellow solution was stirred at −78° C. for 0.5 h, then a solution of 3-methoxy-5H-dibenzo[a,d]cycloheptene-10(11H)-one (715 mg, 3 mmol) in dry THF (3 mL) was added dropwise over 3 min. Additional dry THF (0.4 mL) was used in transfer. After 0.5 h at −78° C., the reaction was quenched with saturated NH$_4$Cl (15 mL), warmed to RT, and extracted with EtOAc (2×30 mL). Drying (MgSO$_4$), concentration, and chromatography (silica gel, 10% EtOAc/hexanes (400 mL), then 20% EtOAc/hexanes) gave recovered 3-methoxy-5H-dibenzo[a,d]cycloheptene-10(11H)-one (305.4 mg, 43%) as a yellow solid, followed by the title compound as a light yellow oil (531.9 mg, 54%): TLC R$_f$ 0.37 (20% EtOAc/hexanes); $^1$H NMR (250 MHz, CDCl$_3$) δ 7.63 (d, J=7.7 Hz, 1H), 7.00–7.30 (m, 4H), 6.80 (d, J=2.6 Hz, 1H, 6.69 (dd, J=8.2, 2.6 Hz, 1H), 3.95–4.35 (m, 2H), 4.07 (s, 2H), 3.76 (s, 3H), 3.68 (s, 1H), 3.64 (d, J=14.2 Hz, 1H), 3.35 (d, J=14.2 Hz, 1H), 2.79 (d, J=16.0 Hz, 1H), 2.66 (d, J=16.0 Hz, 1H), 1.22 (t, J=7.2 Hz, 3H); FTIR (CCl$_4$) 3580 (sharp), 3509 (broad), 1735, 1715, 1503, 1261, 1198, 1156, 1044 cm$^{-1}$; MS (ES) m/e 675.2 (2M+Na)$^+$, 653.2 (2M+H)$^+$.

f) Ethyl (±)-10,11-dihydro-3-methoxy-5H-dibenzo[a,d] cycloheptene-10-acetate

10% Pd/C (242 mg, 0.23 mmol) was added to a solution of ethyl (±)-10,11-dihydro-10-hydroxy-3-methoxy-5H-dibenzo [a,d]cycloheptene-10-acetate (741.1 mg, 2.27 mmol) and conc. HCl (0.19 mL, 2.27 mmol) in glacial AcOH (23 mL), and the mixture was shaken on a Parr apparatus at RT under H$_2$ (50 psi). After 6 h, the reaction was filtered through celite®, and the filter pad was washed with EtOAc. The filtrate was concentrated, and the residue was reconcentrated from toluene. The resulting faintly yellow, oily residue was chromatographed (silica gel, 20% EtOAc/hexanes) to afford the title compound as a colorless oil (643.6 mg, 91%): TLC R$_f$ 0.57 (20% EtOAc/hexanes); $^1$H NMR (250 MHz, CDCl$_3$) δ 7.05–7.22 (m, 4H), 7.01 (d, J=8.2 Hz, 1H), 6.76 (d, J=2.7 Hz, 1H), 6.67 (dd, J=8.2, 2.7 Hz, 1H), 4.30 (d, J=15.0 Hz, 1H), 4.11–4.25 (m, 2H), 3.85 (d, J=15.0 Hz, 1H), 3.70–3.90 (m, 1H), 3.77 (s, 3H), 3.31 (dd, J=15.0, 4.1 Hz, 1H), 2.93 (dd, J=15.0, 9.2 Hz, 1H), 2.64 (dd, J=15.6, 5.0 Hz, 1H), 2.52 (dd, J=15.6, 9.3 Hz, 1H), 1.27 (t, J=7.1 Hz, 3H); FTIR (CCl$_4$) 1734, 1611, 1504,1285, 1263, 1155, 1044 cm$^{-1}$; MS (ES) m/e 333.0 (M+Na)$^+$, 328.0 (M+NH$_4$)$^+$, 311.0 (M+H)$^+$, 265.0 (M+H-EtOH)$^+$.

g) Ethyl (±)-10,11-dihydro-3-hydroxy-5H-dibenzo[a,d] cycloheptene-10-acetate

Anhydrous AlCl$_3$ (1.38 g, 10.35 mmol) was added all at once to a solution of ethyl (±)-10,11-dihydro-3-methoxy- 5H-dibenzo[a,d]cycloheptene-10-acetate (643.6 mg, 2.07 mmol) in anhydrous $CH_2Cl_2$ (21 mL) at 0° C. under argon. The yellow solution was warmed to RT and stirred for 3 h, then was cooled to 0° C. and quenched with cold 3 N HCl (10 mL). The layers were separated, and the aqueous layer was extracted with $CH_2Cl_2$. The combined organic layers were dried ($MgSO_4$) and concentrated. Silica gel chromatography (25% EtOAc/hexanes) gave the title compound as a nearly colorless oil (611.7 mg, 100%): TLC $R_f$ 0.26 (20% EtOAc/hexanes); $^1H$ NMR (400 MHz, $CDCl_3$) δ 7.03–7.22 (m, 4H), 6.93 (d, J=8.1 Hz, 1H), 6.69 (d, J=2.6 Hz, 1H), 6.58 (dd, J=8.1, 2.6 Hz, 1H), 5.00 (s, 1H), 4.25 (d, J=14.9 Hz, 1H), 4.11–4.25 (m, 2H), 3.73–3.88 (m, 1H), 3.79 (d, J=14.9 Hz, 1H), 3.28 (dd, J=15.0, 4.1 Hz, 1H), 2.91 (dd, J=15.0, 9.3 Hz, 1H), 2.65 (dd, J=15.6, 4.9 Hz, 1H), 2.53 (dd, J=15.6, 9.5 Hz, 1H), 1.27 (t, J=7.2 Hz, 3H); FTIR ($CCl_4$) 3611 (sharp), 3447 (broad), 1734, 1504, 1291, 1272, 1176, 1152 $cm^{-1}$; MS (ES) m/e 314.2 $(M+NH_4)^+$, 297.2 $(M+H)^+$.

h) Ethyl (±)-10,11-dihydro-3-(trifluoromethanesulfonyloxy)-5H-dibenzo[a,d]cycloheptene-10-acetate Trifluoromethanesulfonic anhydride (0.45 mL, 2.68 mmol) was added dropwise to a solution of ethyl (±)-10,11-dihydro-3-hydroxy-5H-dibenzo[a,d]cycloheptene-10-acetate (611.7 mg, 2.06 mmol) and 2,6-lutidine (0.48 mL, 4.12 mmol) in anhydrous $CH_2Cl_2$ (10.3 mL) at −78° C. under argon. After 0.5 h, the reaction was warmed to RT and stirred for 1 h. The yellow solution was diluted with $Et_2O$ (50 mL) and washed sequentially with 1.0 N HCl (5 mL), 5% $NaHCO_3$ (5 mL), and brine (5 mL). Drying ($MgSO_4$), concentration, and silica gel chromatography (20% EtOAc/hexanes) gave the title compound as a colorless oil (808.9 mg, 92%): TLC $R_f$ (20% EtOAc/hexanes) 0.58; $^1H$ NMR (250 MHz, $CDCl_3$) δ 6.98–7.30 (m, 7H), 4.35 (d, J=15.2 Hz, 1H), 4.19 (q, J=7.1 Hz, 2H), 3.91 (d, J=15.2 Hz, 1H), 3.78–3.95 (m, 1H), 3.37 (dd, J=15.2, 4.1 Hz, 1H), 3.02 (dd, J=15.2, 9.6 Hz, 1H), 2.70 (dd, J=15.8, 4.8 Hz, 1H), 2.53 (dd, J=15.8, 9.6 Hz, 1H), 1.27 (t, J=7.1 Hz, 3H); FTIR ($CCl_4$) 1735, 1493, 1427, 1250, 1215, 1144,961, 856 $cm^{-1}$; MS (ES) m/e 451.1 $(M+Na)^+$, 446.2 $(M+NH_4)^+$, 429.2 $(M+H)^+$.

i) Ethyl (±)-10,11-dihydro-3-carboxy-5H-dibenzo[a,d]cycloheptene-10-acetate

A mixture of ethyl (±)-10,11-dihydro-3-(trifluoromethanesulfonyloxy)-5H-dibenzo[a,d]cycloheptene-10-acetate (808.9 mg, 1.89 mmol), KOAc (742 mg, 7.56 mmol), $Pd(OAc)_2$ (21.2 mg, 0.095 mmol), 1,1'-bis(diphenylphosphino)ferrocene (210 mg, 0.38 mmol), and anhydrous DMSO (11 mL) was purged with carbon monoxide (three evacuation/CO flush cycles, followed by bubbling CO through the mixture for 5 min), then was stirred under a balloon of CO in an oil bath set at 70° C. After 3.5 h, the reaction was diluted with $H_2O$ (11 mL), cooled to 0° C., and acidified with 1.0 N HCl (ca. 8 mL). $CH_2Cl_2$ extraction (3×30 mL), drying ($Na_2SO_4$), concentration, and reconcentration from toluene left a reddish-orange liquid (2–3 mL). Chromatography (silica gel, 3:2:0.1 EtOAc/toluene/AcOH; mixed fractions again with 1:1:0.1 EtOAc/toluene/AcOH) gave the title compound (581.9 mg, 95%) as a viscous, yellow oil which partially crystallized in high vacuum at 40° C.: TLC $R_f$ (3:2:0.1 EtOAc/toluene/AcOH) 0.60; $^1H$ NMR (250 MHz, $CDCl_3$) δ 7.95 (d, J=1.5 Hz, 1H), 7.87 (dd, J=7.8, 1.5 Hz, 1H), 7.00–7.35 (m, 5H), 4.40 (d, J=15.2 Hz, 1H), 4.19 (q, J=7.1 Hz, 2H), 3.97 (d, J=15.2 Hz, 1H), 3.28–4.00 (m, 1H), 3.43 (dd, J=15.3, 4.0 Hz, 1H), 3.07 (dd, J=15.3, 9.5 Hz, 1H), 2.69 (dd, J=15.8, 4.8 Hz, 1H), 2.53 (dd, J=15.8, 9.5 Hz, 1H), 1.28 (t, J=7.1 Hz, 3H); FTIR ($CCl_4$) 2357–3378 (broad), 1735, 1692, 1280 $cm^{-1}$; MS (ES) m/e 342.2 $(M+NH_4)^+$, 325.2 $(M+H)^+$, 307.2 $(M+H−H_2O)^+$.

PREPARATION 2

Preparation of Ethyl 2-Carboxy-10,11-dihydro-5H-dibenzo[a,d]cycloheptenyl-10-acetate a) Methyl 2-Benzoyl-5-methoxyphenylacetate Methyl 3-methoxy-phenylacetate was treated with benzoyl chloride and aluminum chloride as described in *J. Chem. Soc., Perkin Trans I* 1991, 171 to give the title compound.

b) Methyl 2-Benzyl-5-methoxyphenylacetate

The compound of Preparation 2(a) is treated with sodium borohydride and trifluoroacetic acid in dichloromethane according to the general procedure of Synthesis 1978, 763, to give the title compound.

c) 2-Benzyl-5-methoxyphenylacetic Acid

The compound of Preparation 2(b) is treated with aqueous sodium hydroxide and methanol and stirred. The mixture is concentrated and treated with dilute hydrochloric acid to give the title compound.

d) 5,11-Dihydro-2-methoxy-10H-dibenzo[a,d]cyclohepten-10-one

The compound of Preparation 2(c) is added to a mixture of phosphoric acid and phosphorous pentoxide stirred and heated to 80° C. according to the general procedure of U.S. Pat. No. 3,567,730 to give the title compound.

e) 5,11-Dihydro-2-hydroxy-10H-dibenzo[a,d]cyclohepten-10-one

The compound of Preparation 2(d) is treated with ethanethiol and aluminum chloride according to the general procedure of Tetrahedron. Letters 1978, 5211 to give the title compound.

f) 5,11-Dihydro-2-(trifluoromethanesulfonyl)oxy-10H-dibenzo[a,d]cyclohepten-10-one The compound of Preparation 2(e) is treated with triflic anhydride according to the general procedure of *J. Chem. Soc., Chem. Commun.* 1987, 904 to give the title compound.

g) 5,11-Dihydro-2-methoxycarbonyl-10H-dibenzo[a,d]cyclohepten-10-one

The compound of Preparation 2(f) is treated with carbon monoxide, methanol, palladium acetate and 1,3-bis(diphenylphosphino)propare in dimethyl sulfoxide according to the general procedure of *J. Chem. Soc., Chem. Commun.* 1987, 904 to give the title compound.

h) 5,11-Dihydro-2-carboxy-10H-dibenzo[a,d]cyclohepten-10-one

The compound of Preparation 2(g) is stirred with dilute aqueous sodium hydroxide. The mixture is treated with dilute hydrochloric acid to give the title compound.

i) 5,11-Dihydro-2-tert-butoxycarbonyl-10H-dibenzo[a,d]cyclohepten-10-one

The compound of Preparation 2(h) is treated with N,N-dimethylformamide di-tert-butyl acetal accoding to the general procedure of *Synthesis* 1983, 2, 135 to give the title compound.

j) Ethyl 2-tert-Butoxycarbonyl-5H-dibenzo[a,d]cycloheptene-10-acetate

The compound of Preparation 2(i) is treated with zinc powder and ethyl bromoacetate according to the general procedure of *Org. Reactions* 1947, 1, and *J. Am. Chem. Soc.* 1938, 60, 2947 to give the title compound.

k) Ethyl 2-Carboxy-5H-dibenzo[a,d]cycloheptene-10-acetate

The compound of Preparation 2(j) was treated with trifluoroacetic acid in dichloromethane and stirred. The mixture is concentrated to give the title compound.

l) Ethyl 2-Carboxy-10,11-dihydro-5H-dibenzo[a,d]cycloheptene-10-acetate

Using the general procedure of Example 1(f), except substituting the compound of Preparation 2(k) for the compound of Preparation 1 (e), gives the title compound.

PREPARATION 3

Preparation of Ethyl 7-Carboxy-9.10 dihydro-4H-benzo[4,5]cyclohepta[1,2-b]furan-10-acetate Using the procedure of Preparation 2, except substituting 3-furoyl chloride for benzoyl chloride, gives the title compound.

PREPARATION 4

Preparation of Methyl 8-Carboxy-10,11-dihydro-5H-tetrazolo[5,1-c][1,4]-benzodiazepine-11-acetate a) tert-Butyl 4-[N-(tert-Butoxycarbonyl)-N-(methoxycarbonyl)aminomethyl]-3-nitrobenzoate To a solution of tert-butyl 4-bromomethyl-3-nitrobenzoate (2.27 g, 7.2 mmol) (*Int. J. Peptide Res.* 1990, 36, 31) in dimethylformamide (25 mL) was added a suspension of potassium tert-butyl methyl iminodicarboxylate (*J.C.S. Perkin I* 1977, 1088-90) (1.56 g, 7.3 mmol) in dimethylformamide (20 mL). The dark brown solution was stirred 1 h and poured into water (400 mL), extracted with ethyl acetate (3×100 mL) and the combined organic layers were washed with water (5×75 mL), dried (sodium sulfate) and concentrated to give a pale orange oil which was purified by flash chromatography on silica gel (20% ethyl acetate/hexane) to give the title compound (2.15 g, 73%): $^1$H NMR (400 MHz, CDCl$_3$) δ 8.65 (s, 1H), 8.2 (d, 1H), 7.45 (d, 1H), 5.3 (s, 2H), 3.8 (s, 3H), 1.6 (s, 9H), 1.45 (s, 9H).

b) tert-Butyl 4-[N-(tert-Butoxycarbonyl)aminomethyl]-3-nitrobenzoate

The compound of Preparation 4(a) (2.15 g, 5.24 mmol) was dissolved in a mixture of methanol (120 mL) and 0.95 N sodium hydroxide (15 mL). After 15 min, acetic acid (3.0 mL) was added and mixture was concentrated. The residue was dissolved in ethyl acetate (300 mL) and extracted with water (3×75 mL). The organic layer was washed with brine (75 mL), dried (sodium sulfate) and concentrated to give a yellow oil which was purified by chromatography on silica gel (20% ethyl acetate/hexane) to give the title compound (1.0 g, 54%): $^1$H NMR (400 MHz, CDC$_3$) δ 8.6 (s, 1H), 8.2 (d, 1H), 7.7 (d, 1H), 5.35 (m, 1H), 4.6 (d, 2H), 1.65 (s, 9H), 1.4 (s, 9H).

c) tert-Butyl 3-Amino-4-[N-(tert butoxycarbonyl)aminomethyl]benzoate

A solution of the compound of Preparation 4(b) (0.80 g, 2.27 mmol) in ethanol (100 mL) containing 10% palladium on carbon (0.5 g) was hydrogenated (40 psi). After 30 min, the mixture was filtered and concentrated to give the title compound (0.72 g, 100%): $^1$H NMR (400 MHz, CDCl$_{13}$) δ 7.25 (m, 2H), 7.1 (d, 1H), 4.9 (b, 1H), 4.25 (d, 2H), 1.6 (s, 9H), 1.45 (s, 9H).

d) tert-Butyl (E,Z)-4-[N-(tert-Butoxycarbonyl)aminomethyl]-3-[2-(1,4-dimethoxy-1,4-dioxo-2-butenyl)amino]benzoate A mixture of the compound of Preparation 4(c) (0.7 g, 2.2 mmol) and dimethyl acetylenedicarboxylate (0.37 g, 2.6 mmol) in methanol (40 mL) was heated to reflux for 30 min, cooled and concentrated. The residue was purified by flash chromatography (silica gel, 20% ethyl acetate/hexane) to yield the title compound (0.7 g, 70%): $^1$H NMR (400 MHz, CDCl$_3$) δ 9.6 (s, 1H), 7.7 (d, 1H), 7.35 (m, 2H), 5.5 (s, 1H), 5.0 (b, 1H), 4.4 (d, 2H), 3.75 (s, 3H), 3.7 (s, 3H), 1.6 (s, 9H), 1.45 (s, 9H).

e) tert-Butyl 4-[N-(tert-Butoxycarbonyl)aminomethyl]-3-[2-(1,4-dimethoxy-1,4-dioxo-2-butyl)amino]benzoate The compound of Preparation 4(d) (0.68 g, 1.5 mmol) and 10% palladium on carbon (0.5 g) in methanol (70 mL) was shaken in a hydrogen atmosphere (40 psi) for 1 h. The mixture was filtered and concentrated to yield the title compound (0.66 g, 95%): $^1$H NMR (400 MHz, CDCl$_{13}$) δ 7.8 (d, 1H), 7.75 (s, 1H), 7.1 (d, 1H), 5.4 (b, 1H), 4.9 (b, 1H), 4.6 (m, 1H), 4.3 (m, 2H), 3.7 (s, 3H), 3.65 (s, 3H), 2.9 (m, 2H), 1.6 (s, 9H), 1.45 (s, 9H)

f) 4-(Aminomethyl)-3-[2-(1,4-dimethoxy-1,4-dioxo-2-butyl)amino]benzoic Acid

The compound of Preparation 4(e)(0.66 g, 1.4 mmol) in methylene chloride (10 mL) and trifluoroacetic acid (10 mL) was kept at room temperature for 1 h and concentrated to yield the title compound.

g) Methyl (R,S)-8-Carboxy-2,3,4,5-tetrahydro-3-oxo-1H-1,4-benzodiazepine-2-acetate The compound of Preparation 4(f) was dissolved in methanol (60 mL) and treated with a solution of 25% sodium methoxide in methanol(0.73 mL, 3.2 mmol) and warmed to 50° C. for 1 h. The mixture was acidified with 1N hydrogen chloride in ether (3.5 mL) and concentrated to yield the title compound (0.44 g, 98%): $^1$H NMR (400 MHz, DMSO-d$_6$) δ 8.15 (t, 1H), 7.2 (s, 1H), 7.1 (d, 1H), 7.05 (d, 1H), 5.0 (dd, 1H), 4.9 (m, 1), 3.75 (dd, 1H), 3.6 (s, 3H), 2.8 (dd, 1H), 2.6 (dd, 1H).

h) Methyl (R,S)-8-Carboxy-10,11-dihydro-5H-tetrazolo[5,1-c][1,4]-benzodiazepine-11-acetate The compound of Preparation 4(g) is treated with triphenylphosphine, diethyl azodicarboxylate and trimethylsilyl azide in tetrahydrofuran according to the general procedure of *J. Org. Chem.* 1991, 56, 2395 to yield the title compound.

PREPARATION 5

Preparation of Methyl (R,S)-8-carboxy-10,11-dihydro-5H-imidazo [2,1-c][1,4]benzodiazepine-11-acetate a) Methyl (R,S)-8-Carboxy-2,3,4,5-tetrahydro-3-thioxo-1H-1,4-benzodiazepine-2-acetate The compound of Preparation 4(g) is treated with Lawesson's reagent according to the general procedure of *Tet. Lett.* 1980, 21, 4061 to give the title compound.

b) Methyl (R,S)-8-Carboxy-2,5-dihydro-3-methylthio-1H-1,4-benzodiazepine-2-acetate The compound of Preparation 5(a) is treated with iodomethane according to the general procedure of *Tetrahedron* 1960, 517 to give the title compound.

c) Methyl (R,S)-8-Carboxy-2,5-dihydro-3-[(2,2-dimethoxyethyl)amino]-1H-1,4-benzodiazepine-2-acetate The compound of Preparation 5(b) is treated with aminoacetaldehyde dimethylacetal according to the general procedure of *J. Heterocyclic Chem.* 1989, 26, 205 to give the title compound.

d) Methyl (R,S)-8-Carboxy-10,11-dihydro-5H-imidazo[2,1-c][1,4]benzodiazepine-11-acetate The compound of Preparation 5(c) is treated with aqueous trifluoroacetic acid to give the title compound.

PREPARATION 6

Preparation of Ethyl (R,S)-2-Amino-10,11-dihydro-5H-dibenzo[a,d]cycloheptene-10-acetate a) Ethyl 2-Benzyloxycarbonylamino-5H-dibenzo[a,d]cycloheptene-10-acetate A mixture of the compound of Preparation 2(k), triethylamine and diphenyl phosphorylazide in toluene is heated. The resulting mixture is treated with benzyl alcohol, stirred and concentrated. The residue is chromatographed on silica gel the title compound.

b) Ethyl (R,S)-2-Amino-10,11-dihydro-5H-dibenzo[a,d]cycloheptenyl-10-acetate

The compound of Preparation 6(a) is dissolved in methanol and treated with 10% palladium on carbon and 1M hydrogen chloride in ether and the mixture is shaken in a hydrogen atmosphere. The mixture is filtered and concentrated to yield the title compound.

PREPARATION 7

Preparation of 2-[1-[4-(Benzyloxycarbonyl)piperazinyl]]-N-methyl-ethanamine a) 2-[1-[4-(Benzyloxycarbonyl)piperazinyl]]ethanamine 2-(1-Piperazinyl)ethylamine was protected according to the general procedure of *Tet. Lett.* 1986, 27 4391. A solution of tert-butylchlorodiphenylsilane (7.8 mL, 30 mmol) in acetonitrile (10 mL) was added dropwise to a solution of 2-(1-piperazinyl)ethylamine (4.0 mL, 31 mmol) and triethylamine (6.3 mL, 45 mmol) in acetonitrile (20 mL) stirred at 10° C. The mixture was stirred 2 h at RT, cooled to 10° C. and treated with triethylamine (6.3 mL, 45 mmol) and a solution of benzyl chloroformate (4.3 mL, 30 mmol) in dichloromethane (10 mL). The mixture was stirred at RT for 2 h, filtered and concentrated. The residue was stirred in 80% acetic acid (100 mL) overnight, poured into brine and washed with ethyl acetate. The aqueous phase was basified with saturated sodium carbonate, extracted with ethyl acetate and the organic phase was dried (magnesium sulfate), filtered and concentrated to give the title compound (1.1 g, 14%): $^1$NMR (400 MHz, CDCl$_3$) δ 2.43 (6H, m), 2.80 (2H, m), 3.52 (4H, m), 5.14 (2H, s), 7.38 (5H, s).

b) 2-[1-[4-(Benzyloxycarbonyl)piperazinyl]]-N-methyl-ethanamine

Formic acid (0.5 mL, 12.2 mmol) was added dropwise via syringe to acetic anhydride (1.0 mL, 9.8 mmol) at 10° C. The mixture was stirred for 10 min and heated to 50° C. for 2 h. The mixture was cooled to RT, anhydrous tetrahydrofuran (10 mL) was added followed by the compound of Preparation 7(a) (1.0 g, 3.8 mmol) dissolved in tetrahydrofuran. The mixture was stirred for 2.5 h at RT, concentrated and the residue was dissolved in tetrahydrofuran (25 mL) and cooled to 10° C. 1.0M Boron methyl sulfide (1 mL, 10 mmol) dissolved in tetrahydrofuran (10 mL) was added dropwise at 10° C. The mixture was stirred until gas evolution ceased and was heated to reflux for 2 h. The mixture was cooled, treated carefully with saturated methanolic hydrogen chloride (20 mL) and heated to reflux for 1 h. The mixture was concentrated to yield the title compound (400 mg, 40%): MS (ES) m/e 278.0 [M+H]$^+$; $^1$NMR (400 MHz, CDCl$_3$) δ 2.68–3.92 (15H, m), 5.15(2H, s), 7.37 (5H, s).

PREPARATION 8

Preparation of 4-[N-(Benzyloxycarbonyl)-(aminoiminomethyl)]benzoyl Chloride

A mixture of 4-[N-(benzyloxycarbonyl)-(aminoiminomethyl)]benzoic acid (0.23 g, 1.0 mmol) and thionyl chloride (3 mL) in dichloromethane (3 mL) was heated to reflux for 10 min, concentrated, treated with toluene and concentrated several times to give the title compound.

PREPARATION 9

Preparation of N-(t-butoxycarbonyl)-4,4'-bipiperidine 4,4'-Bipiperidine dihydrochloride (2.5 g, 10 mmol) was dissolved in water (10 mL) and treated with 5N sodium hydroxide to pH 8–9, diluted to 120 mL with ethanol and stirred at RT. The resulting mixture was treated with di-t-butyl dicarbonate (2.4 g, 11 mmol) in ethanol (80 mL) in one portion and the mixture stirred at RT, with periodic additions of 5N sodium hydroxide to maintain a pH of 8–9. After 5 h. the mixture was concentrated and the residue was dissolved in a mixture of 1:1 ether:water (100 mL) and the pH adjusted to 12 with 5N sodium hydroxide. The aqueous phase was extracted with ether and the organic phase was washed sequentially with brine, dilute citric acid, and water. The aqueous phase was adjusted to pH 12–13 with 5N sodium hydroxide and extracted with ether. The organic phase was washed with brine, dried (sodium sulfate), concentrated to a clear oil and dried in vacuo to give the title compound (1.7 g, 63%) as a solid. TLC R$_f$ 0.4 (Kieselgel 60 F$_{254}$, 15:3:2 2-butanol:formic acid:water); MS (ES) m/e 268.3 [M+H]$^+$.

PREPARATION 10

Preparation of 2-(Methylaminomethyl)benzimidazole dihydrochloride a) 2-[(tert-Butoxycarbonyl)sarcosyl]aminoaniline A solution of phenylenediamine (100 g, 0.924 mole) and Boc-sarcosine (175 g, 0.924 mole) in DMF (1750 mL) was cooled to −10° C. under argon, and a solution of DCC (190.8 g, 0.924 mole) in CH$_2$Cl$_2$ (1750 mL) was added in a slow stream over 1 hr. The temperature rose to 0° C. during the addition. The reaction was stirred overnight while the temperature was allowed to rise to RT. The white precipitate was removed by filtration, and the filtrate was diluted with H$_2$O (3.5 L) and saturated brine (1 L). The CH$_2$Cl$_2$ layer was separated and the aqueous phase was extracted with EtOAc (2×1 L). The combined organic layers were washed with H$_2$O (1 L) and brine (0.5 L), then were concentrated to a yellow residue (341 g). This was triturated with EtOAc to afford the title compound (179.4 g, 70%): mp 134–136° C.

b) 2-[(N-tert-Butoxycarbonyl-N-methyl)aminomethyl]benzimidazole

A solution of 2-[(tert-butoxycarbonyl)sarcosyl]aminoaniline (178.4 g, 0.639 mole) in THF (900 mL) and AcOH (900 mL) was heated to reflux under argon for 1 hr, then a vacuum was carefully applied to the reaction, and most of the THF was removed by distillation. The residual solution was poured into stirred ice water, and conc. NH$_4$OH (1150 mL) was added to adjust the pH to 10. An oil formed which crystallized on stirring overnight. The solid was filtered and dried at 50° C. at atmospheric pressure for two days to leave a yellow-white solid (167 g, 100%): mp 140–150° C. Further drying at RT and atmospheric pressure gave the crude title compound (162 g, 97%).

b) 2-(Methylaminomethyl)benzimidazole dihydrochloride

A solution of 4 M HCl/dioxane (616 mL, 2.46 mole) and anisole (134 mL, 1.23 mole) was cooled to 0° C. under argon, and a solution of 2-[(N-tert-butoxycarbonyl-N-methyl)aminomethyl]benzimidazole (161 g, 0.616 mole) in CH$_2$Cl$_2$ (800 mL) was added in a slow stream over 30 min. The temperature rose to 8° C. during the addition, and a white precipitate began to form before the addition was complete. The reaction was stirred for 20 min, then the title compound (66.6 g, 46%) was collected by filtration: mp 250–255° C. (dec.). Anal. Calcd for C$_9$H$_{11}$N$_3$.2 HCl: C, 46.17; H, 5.60; N, 17.95. Found: C, 46.33; H, 5.68; N, 17.55. The filtrate was diluted with Et$_2$O, and the mixture was allowed to stand overnight. Filtration gave additional title compound (62 g; total yield 128.6 g, 89%) as a pink solid: mp 248–253° C. (dec.).

PREPARATION 11

Preparation of 2-[(2-aminoethyl)amino]pyridine dihydrochloride a) Mono-Boc-1,2-ethylenediamine A solution of di-tert-butyl dicarbonate (10.91 g, 50 mmole) in $CH_2Cl_2$ (50 mL) was added dropwise over 30 min to a briskly stirred solution of 1,2-ethylenediamine (33 mL, 500 mmole) in $CH_2Cl_2$ (250 mL) at 0° C. under argon. A precipitate separated during the addition. When the addition was complete, the reaction was warmed to RT, stirred for 1 hr, and concentrated on the rotavap. The residue was taken up in $H_2O$ (100 mL) and filtered to remove a small amount of insoluble material. The filtrate was extracted with $CH_2Cl_2$ (3×100 mL), and the combined organics were dried ($MgSO_4$) and concentrated to afford the title compound (6.00 g, 75%) as a cloudy liquid: $^1H$ NMR (250, $CDCl_3$) δ 4.75–5.00 (m, 1 H), 3.05–3.25 (m, 2 H), 2.65–2.85 (m, 2 H). 1.46 (s, 9 H), 112 (br s, 2 H).

b) 2-[[2-(Boc-amino)ethyl]amino]pyridine-N-oxide

A mixture of mono-Boc-1,2-ethylenediamine (5.83 g, 36.39 mmole), 2-chloropyridine-N-oxide hydrochloride (7.25 g, 43.67 mmole), $NaHCO_3$ (15.29 g, 182 mmole), and tert-amyl alcohol (36 mL) was heated at reflux. After 47 hr, the dark brown mixture was cooled, diluted with $CH_2Cl_2$ (100 mL), and suction filtered to remove insoluble materials. The filtrate was concentrated and reconcentrated from toluene. Silica gel chromatography (10% MeOH/$CHCl_3$) gave impure title compound (8.23 g, 89%) as a yellow solid which was used without further purification: TLC (10% MeOH/$CHCl_3$) $R_f$ 0.42; $^1H$ NMR (250, $CDCl_3$) δ 8.16 (dd, J=6.5, 1.3 Hz, 1 H), 7.05–7.30 (m, 2 H), 6.68 (br d, J=8.6 Hz, 1 H), 6.50–6.65 (m, 1 H), 5.70–5.95 (m, 1 H), 3.35–3.60 (m, 4 H), 1.44 (s, 9 H); MS (ES) m/e 254 $(M+H)^+$.

c) 2-[[2-(Boc-amino)ethyl]amino]pyridine

10% Pd/C (106.4 mg, 0.10 mmole) was added to a solution of 2-[[2-(Boc-amino)ethyl]amino]pyridine-N-oxide (126.7 mg, 0.5 mmole) and cyclohexene (0.25 mL, 0.25 mmole) in absolute EtOH (5 mL), and the mixture was heated to reflux. After 16 hr, the reaction was filtered through celite® and the filtrate was concentrated. The residue was combined with the residue obtained from a separate preparation (0.5 mmole scale), and the combined materials were purified by silica gel chromatography (5% MeOH/$CHCl_3$). The title compound (148.4 mg, 63% based on 1 mmole of 2-[[2-(Boc-amino)ethyl]amino]pyridine-N-oxide) was obtained as a yellow oil: TLC (5% MeOH/$CHCl_3$) $R_f$ 0.43; $^1H$ NMR (400, $CDCl_3$) δ 8.05–8.12 (m, 1 H), 7.37–7.46 (m, 1 H), 6.53–6.61 (m, 1 H), 6.41 (d, J=8.3 Hz, 1 H), 5.12 (br s, 1 H), 4.86 (br s, 1 H), 3.26–3.51 (m, 4 H), 1.44 (s, 9 H); MS (ES) m/e 238 $(M+H)^+$.

d) 2-[(2-Aminoethyl)amino]pyridine dihydrochloride

4N HCl in dioxane (3.2 mL) was added in a stream to a solution of 2-[[2-(Boc-amino)ethyl]amino]pyridine (148.4 mg, 0.63 mmole) in anhydrous $CH_2Cl_2$ (3.2 mL) at 0° C., then the reaction was warmed to RT. After 2 hr, the mixture was suction filtered to collect the precipitated solid, which was washed with anhydrous $Et_2O$ and dried to afford the title compound (132.8 mg, quantitative) as a yellow solid: $^1H$ NMR (400, $CD_3OD$) δ 7.99–8.07 (m, 1 H), 7.92–7.98 (m, 1 H), 7.19 (d, J=9.1 Hz, 1 H), 6.98–7.04 (m, 1 H) 3.76 (t, J=6.2 Hz, 2 H), 3.27 (t, J=6.2 Hz, 2 H, partially obscured by residual solvent signal); MS (ES) m/e 138 $(M+H)^+$.

PREPARATION 12

Preparation of 2-[(3-hydroxy-1-propyl)amino]pyridine-N-oxide a) 2-[(3-Hydroxy-1-propyl)amino]pyridine-N-oxide A mixture of 2-chloropyridine-N-oxide (16.6 g, 0.1 mole), 3-amino-1-propanol (15.3 mL, 0.2 mole), $NaHCO_3$ (42 g, 0.5 mole), and tert-amyl alcohol (100 mL) was heated to reflux. After 21 hr, the reaction was cooled, diluted with $CH_2Cl_2$ (300 mL), and suction filtered to remove insoluble materials. The filtrate was concentrated and reconcentrated from toluene to leave a yellow oil. Silica gel chromatography (20% MeOH/$CHCl_3$) gave the title compound (15.62 g, 93%) as a yellow solid: TLC (20% MeOH/$CHCl_3$) $R_f$ 0.48; $^1H$ NMR (250, $CDCl_3$) δ 8.07 (dd, J=6.6, 1.2 Hz, 1 H), 7.34 (br t, 1 H), 7.10–7.30 (m, 1 H), 6.64 (dd, J=8.5, 1.4 Hz, 1 H), 6.40–6.60 (m, 1 H), 4.49 (br s, 1 H), 3.65–3.90 (m, 2 H), 3.35–3.60 (m, 2 H), 1.75–2.00 (m, 2 H); MS (ES) m/e 169 $(M+H)^+$.

PREPARATION 13

Methyl 3-carboxy-10,11-dihydro-5-methyl-dibenzo[b,f]azepine-10-acetate a) 5-Methoxy-2-(methoxycarbonyl)diphenylamine 5-Methoxy-2-(carboxy)diphenylamine, prepared as described in *Chem. Ber.* 1956, 89, 2174–2190, is treated with hydrogen chloride in methanol, to afford the title compound.

b) 5,11-Dihydro-3-methoxy-5-methyl-10-dibenzo[b,f]azepin-10-one

Using the general procedure of NL 7011296, except substituting the compound of Preparation 13(a) for 5-chloro-2-(methoxycarbonyl)diphenylamine, gives the title compound.

c) Methyl 3-carboxy-10,11-dihydro-5-methyl-dibenzo[b,f]azepine-10-acetate

Using the procedure of Preparation 1(e–i), except substituting the compound of Preparation 13(b) for the compound of Preparation 1(d), gives the title compound.

PREPARATION 14

Methyl 3-carboxy-10,11-dihydro-dibenzo[b,f]oxepine-10-acetate a) 3-Methoxy-dibenzo[b,f]oxepin-10(11H)-one Using the general procedure of *J. Heterocycl. Chem.* 1986, 23, 265–9, except substituting phenol for 4-fluorophenol, gives the title compound.

b) Methyl 3-carboxy-10,11-dihydro-dibenzo[b,f]oxepine-10-acetate

Using the procedure of Preparation 1(e–i), except substituting the compound of Preparation 14(a) for the compound of Preparation 1(d), gives the title compound.

PREPARATION 15

Methyl 3-carboxy-10,11-dihydro-dibenzo[b,f]thiepine-10-acetate

Using general procedure of Preparation I (e–i), except substituting 3-methoxy-dibenzo[b,f]thiepin-10(11H)-one, prepared as described in *Collect. Czech. Chem. Commun.* 1979, 44, 2108–23, for the compound of Preparation 1(d), gives the title compound.

PREPARATION 16

Methyl 2-carboxy-6,11-dihydro-5H-dibenz[b,e]azepine-6-acetate a) 2-Benzy-4-bromo-N-(formyl)aniline Using the general procedure of *Coll. Czech. Chem. Commun.* 1965, 30, 1163–1172, 2-benzyl-4-bromo-aniline, prepared as in *Khim. Geterotsikl. Soedin.* 1983, 3, 411–414, is heated with ethyl formate to afford the title compound.

b) 2-Bromo-11H-dibenz[b,e]azepine

Using the general procedure of *Coll. Czech. Chem. Commun.* 1965, 30, 1163–1172, the compound of Preparation 16(a) is heated in a mixture of polyphosphoric acid and phosphorous oxychloride to afford the title compound.

c) Methyl 2-bromo-6,11-dihydro-5H-dibenz[b,e]azepine-6-acetate

Using the general procedure of *Bull. Chem. Soc. Jpn.* 1990, 63, 3122–3131, the compound of Preparation 16(b) is treated with the t-butyldimethylsilyl ketene acetal of methyl acetate, trimethylsilylcyanide and a catalytic amount of di-$\mu$-chloro-bis( 1,5-cyclooctadiene)-dirhodium ([Rh(COD)Cl]$_2$) in dichloromethane in the cold to afford the title compound.

d) Methyl2-carboxy-6,11-dihydro-5H-dibenz[b,e]azepine-6-acetate

Using the general procedure of Preparation 1(i), except substituting the compound of Preparation 16(c) for the compound of Preparation 1(h), gives the title compound.

PREPARATION 17

Methyl 7-carboxy-10,11-dihydro-5-methyl-5H-dibenzo[b,e][1,4]diazepine-11-acetate a) 2-Amino-5-bromo-N-(methyl)diphenylamine Using the general procedure of *Ann. Chem.* 1898, 303, 322, except substituting N-methyl-aniline for aniline, gives 2-nitro-5-bromo-N-(methyl)diphenylamine which is reduced with stannous chloride to give the title compound.

b) 7-Bromo-5H-dibenzo[b,e][1,4]diazepine

Using the general procedure of *Helv. Chem. Acta* 1964, 47, 1163–72, except substituting the compound of Preparation 17(a) for 2-amino-N-(methyl)diphenylamine, affords the title compound.

c) Methyl 7-bromo-10,11-dihydro-5-methyl-5H-dibenzo[b,e][1,4]diazepine-11-acetate Using the general procedure of Preparation 16(c), except substituting the compound of Preparation 17(b) for the compound of Preparation 16(b), gives the title compound.

d) Methyl 7-carboxy-10,11-dihydro-5-methyl-5H-dibenzo[b,e][1,4]diazepine-11-acetate Using the general procedure of Preparation 1(i), except substituting the compound of Preparation 17(c) for the compound of Preparation 1 (h), gives the title compound.

PREPARATION 18

Methyl 7-carboxy-10,11-dihydro-dibenz[b,f][1,4]oxazepine-11-acetate a) 4-Bromo-N-formyl-2-(phenoxy)aniline Using the general procedure of *J. Chem. Soc., Perkin I* 1976, 1279–1285, 4-bromo-2-(phenoxy)aniline, prepared as described in *J. Chem. Soc.*, 1930, 1202–1208, is heated with formic acid to afford the title compound.

b) 7-Bromo-dibenz[b,f][1,4]oxazepine

Using the general procedure of *J. Chem. Soc., Perkin I* 1976, 1279–1285, the compound of Preparation 18(a) is heated in a mixture of polyphosphoric acid and phosphorous oxychloride to afford the title compound.

c) Methyl 7-bromo-10,11-dihydro-dibenz[b,f][1,4]oxazepine-11-acetate Using the general procedure of Preparation 16(c), except substituting the compound of Preparation 18(b) for the compound of Preparation 16(b), gives the title compound.

d) Methyl 7-carboxy-10,11-dihydro-dibenz[b,f][1,4]oxazepine-11-acetate

Using the general procedure of Preparation 1(i), except substituting the compound of Preparation 18(c) for the compound of Preparation 1(h), gives the title compound.

PREPARATION 19

Methyl 7-carboxy-10,11-dihydro-dibenzo[b,f][1,4]thiazepine-11-acetate a) 2-Phenylthio-4-(bromo)aniline 3-Bromo-6-nitrodiphenyldisulfide, prepared as described in *J. Chem. Soc. B* 1966, 963–72, is reduced with stannous chloride to give the title compound.

b) 7-Bromo-dibenz[b,f][1,4]thiazepine

Using the procedure of *Helv. Chem. Acta* 1964, 47, 1163–72, except substituting the compound of Preparation 19(a) for 2-(phenylthio)aniline, gives the title compound.

c) Methyl7-bromo-10,11-dihydro-dibenz[b,f][1,4]thiazepine-11-acetate

Using the general procedure of Preparation 16(c), except substituting the compound of Preparation 19(b) for the compound of Preparation 16(b), gives the title compound.

d) Methyl 7-carboxy-10,11-dihydro-dibenz[b,f][1,4]thiazepine-11-acetate

Using the general procedure of Preparation 1(i), except substituting the compound of Preparation 19(c) for the compound of Preparation 1(h), gives the title compound.

PREPARATION 20

Methyl 2-carboxy-10,11-dihydro-dibenzo[b,f]oxepine-10-acetate a) 2-Methoxy-dibenzo[b,f]oxepin-10(11H)-one Using the general procedure of *J. Heterocycl. Chem.* 1986, 23, 265–9, except substituting phenol for 4-fluorophenol, gives the title compound.

b) Methyl 2-carboxy-10,11-dihydro-dibenzo[b,f]oxepine-10-acetate

Using the procedure of Preparation 1(e–i), except substituting the compound of Preparation 20(a) for the compound of Preparation 1(d), gives the title compound.

The following compounds illustrate methods for preparing the biologically active compounds of this invention from intermediate compounds such as described in the foregoing Preparations.

EXAMPLE 1

Preparation of (±)-10,11-dihydro-3-[[[1H-benzimidazol-2-yl)methyl]methylamino]carbonyl]-5H-dibenzo[a,d]cycloheptene-10-acetic acid a) Ethyl (±)-10,11-dihydro-3-[[[(1H-benzimidazol-2-yl)methyl]methylamino]carbonyl]5H-dibenzo[a,d]cycloheptene-10-acetate EDC (202.4 mg, 1.06 mmol) was added all at once to a solution of ethyl (±)-10,11-dihydro-3-carboxy-5H-dibenzo[a,d]cycloheptene-10-acetate (285.6 mg, 0.88 mmol), 2-(methylamino)methylbenzimidazole dihydrochloride (247.2 mg, 1.06 mmol), HOBt.H$_2$O (142.7 mg, 1.06 mmol), and diisopropylethylamine (0.61 mL, 3.52 mmol) in anhydrous DMF (4.4 mL) at RT. The reaction was stirred at RT for 16.5 h, then was concentrated on the rotavap (high vacuum). The residue was reconcentrated from xylenes, then was dissolved in H$_2$O (5 mL). EtOAc extraction (2×5 mL), drying (MgSO$_4$), concentration, and chromatography (silica gel, 5% MeOH in 1:1 EtOAc/CHCl$_3$) gave the title compound as a faintly yellow foam (389.2 mg, 95%): TLC R$_f$ (10% MeOH in 1:1 EtOAc/CHCl$_3$) 0.60; $^1$H NMR (400 MHz, CDCl$_3$) δ 7.70–7.80 (m, 1H), 7.40–7.50 (m, 1H), 7.35 (s, 1H), 7.21–7.32 (m, 3H), 7.04–7.21 (m, 5H), 4.76–4.88 (m, 2H), 4.36 (d, J=15.2 Hz, 1H), 4.18 (q, J=7.1 Hz, 2H), 3.90 (d, J=15.2 Hz, 1H), 3.82–3.95 (m, 1H), 3.38 (dd, J=15.4, 4.0 Hz, 1H), 3.11 (s, 3H), 3.03 (dd, J=15.4, 9.5 Hz, 1H), 2.69 (dd, J=15.8, 4.8 Hz, 1H), 2.52 (dd, J=15.8, 9.6 Hz, 1H), 1.27 (t, J=7.1 Hz, 3H); FTIR (CCl$_4$) 2700–3470 (broad), 1735, 1629 (shoulder), 1617, 1484, 1454, 1422, 1397, 1271, 1180, 1157 cm$^{-1}$; MS (ES) m/e 468.2 (M+H)$^+$.

b) (±)-10,11-Dihydro-3-[[[(1H-benzimidazol-2-yl)methyl]methylamino]carbonyl]-5H-dibenzo[a,d]cycloheptene-10-acetic acid, sodium salt 1.0 N LiOH (1.0 mL, 1.0 mmol) was added to a mixture of ethyl (±)-10,11-dihydro-3-[[[(1H-benzimidazol-2-yl)methyl]methylamino]carbonyl]-5H-dibenzo[a,d]cycloheptene-10-acetate (389.2 mg, 0.83 mmol) in THF (4.2 mL) and H$_2$O (3.2 mL), and the resulting yellow solution was stirred at RT for 2 h, at 40° C. for 15 h, then at reflux for 0.5 h. The reaction was then concentrated to dryness on the rotavap, and the residue was dissolved in H$_2$O (4 mL). The solution was washed with Et$_2$O (2×4 mL), and the Et$_2$O layers were discarded. The aqueous layer was filtered to remove particulates, then was neutralized with 1.0N HCl (1.0 mL). The precipitated solid was collected by suction filtration and washed with H$_2$O, then was dissolved in hot 1:1 CH$_3$CN/H$_2$O. The solution was hot filtered to remove an insoluble brown oil, and was allowed to cool to RT. Since the product oiled out, the mixture was concentrated to dryness on the rotavap. The residue was dissolved in MeOH (2 mL), and 5% NaHCO$_3$ (2 mL) was added. The mixture was warmed until a homogeneous solution was produced, then was concentrated to remove the MeOH. ODS chromatography (30% MeOH/H$_2$O), then rechromatography with 1:1 MeOH/H$_2$O), concentration, and lyophilization gave the title compound as a colorless powder (187.5 mg, 45%): HPLC k' 1.47 (Hamilton PRP-1®, 35% CH$_3$CN/H$_2$O-0.1% TFA); $^1$H NMR (400 MHz, CD$_3$OD) Rotameric mixture; 6.80–7.65 (m, 11H), 4.64–5.05 (m, 2H), 3.68–4.41 (m, 3H), 2.87–3.46 (m, 5H), 2.30–2.58 (m, 2H); MS (ES) m/e 440.2 (M+H)$^+$. Anal. Calcd for C$_{27}$H$_{24}$N$_3$O$_3$Na.2.25 H$_2$O: C, 64.60; H, 5.72; N, 8.37. Found: C, 64.52; H, 5.80; N, 8.27.

EXAMPLE 2

Preparation of (±)-10,11-dihydro-3-[1-(4,4'-bipiperidinyl)carbonyl]-5H-dibenzo[a,d]cycloheptene-10-acetic acid a) Ethyl (±)-10,11-dihydro-3-[1-(1'-BOC-4,4'-bipiperidinyl)carbonyl]-5H-dibenzo[a,d]cycloheptene-10-acetate EDC (209.3 mg, 1.09 mmol) was added all at once to a solution of ethyl (±)-10,11-dihydro-3-carboxy-5H-dibenzo[a,d]cycloheptene-10-acetate (296.3 mg, 0.91 mmol), 1-BOC-4,4'-bipiperidine (293 mg, 1.09 mmol), HOBt.H$_2$O (147.6 mg, 1.09 mmol), and diisopropylethylamine (0.32 mL, 1.82 mmol) in anhydrous DMF (4.6 mL) at RT. The reaction was stirred at RT overnight, then was concentrated on the rotavap (high vacuum). The residue was reconcentrated from xylenes, then was dissolved in H$_2$O (5 mL). EtOAc extraction (2×5 mL), drying (MgSO$_4$), concentration, and silica gel chromatography (7:3 EtOAc/hexanes) gave the title compound as a light yellow foam (463.4 mg, 89%): TLC R$_f$ (7:3 EtOAc/hexanes) 0.59; $^1$H NMR (250 MHz, CDCl$_3$) δ 6.94–7.46 (m, 7H), 4.58–4.88 (m, 1H), 4.37 (d, J=15.2 Hz, 1H), 4.19 (q, J=7.1 Hz, 2H), 3.89 (d, J=15.2 Hz, 1H), 3.68–4.30 (m, 4H), 3.38 (dd, J=15.3, 4.1 Hz, 1H), 3.01 (dd, J=15.3, 9.4 Hz, 1H), 2.40–3.09 (m, 5H), 1.45 (s, 9H), 1.27 (t, J=7.1 Hz, 3H), 0.85–1.90 (m, 11H); FTIR (CCl$_4$) 1734, 1694, 1637, 1426, 1171 cm$^{-1}$; MS (ES) m/e 1149.8 (2M+H)$^+$, 597.4 (M+Na)$^+$, 575.4 (M+H)$^+$, 519.4 (M+H-C$_4$H$_8$)$^+$.

b) (±)-10,11-Dihydro-3-[1-(4,4'-bipiperidinyl)carbonyl]-5H-dibenzo[a,d]cycloheptene-10-acetic acid A heterogeneous mixture of ethyl (±)-10,11-dihydro-3-[1-(1'-BOC-4,4'-bipiperidinyl)carbonyl]-5H-dibenzo[a,d]cycloheptene-10-acetate (463.4 mg, 0.81 mmol), 1.0 N LiOH (1.0 mL, 1.0 mmol), THF (4.1 mL), and H$_2$O (3.1 mL) was stirred at 40° C. After 17 h, the homogeneous solution was cooled in ice and acidified with 1.0 N HCl (1.5 mL). CH$_2$Cl$_2$ extraction (3×10 mL), drying (MgSO$_4$), and concentration left an off-white foam. This was dissolved in CH$_2$Cl$_2$ (4.1 mL), and the solution was cooled to 0° C. TFA (4.1 mL) was added all at once, and the reaction was warmed to RT. After 1.5 h, the light yellow solution was concentrated to dryness on the rotavap to leave an oil. ODS chromatography (30% CH$_3$CN/H$_2$O-0.1% TFA), concentration, and lyophilization gave the title compound as a colorless powder (437.2 mg, 86%): HPLC k' 1.91 (Hamilton PRP-1®, 30% CH$_3$CN/H$_2$O-0.1% TFA); $^1$H NMR (400 MHz, CD$_3$OD) δ 7.02–7.29 (m, 7H), 4.53–4.73 (m, 1H), 4.34 (d, J=15.0 Hz, 1H), 3.99 (d, J=15.0 Hz, 1H), 3.65–3.89 (m, 2H), 3.30–3.50 (m, 3H), 2.70–3.15 (m, 5H), 2.68 (dd, J=16.0, 5.2 Hz, 1H), 2.52 (dd, J=16.0, 9.1 Hz, 1H), 1.06–2.09 (m, 10H); MS (ES) m/e 447.2 (M+H)$^+$. Anal. Calcd for C$_{28}$H$_{34}$N$_2$O$_3$.1.5 CF$_3$CO$_2$H.0.75 H2O: C, 59.00; H, 5.91; N, 4.44. Found: C, 58.96; 6.00; N, 4.50.

EXAMPLE 3

Preparation of (±)-10,11-dihydro-3-[3-(2-benzimidazolyl)-1-propyl]-5H-dibenzo[a,d]cycloheptene-10-acetic acid a) 4-(2-Tetrahydropyranyloxy)-1-tributylstannyl-1-butyne A solution of n-butyllithium in hexanes (1.6 M, 18.8 mL, 30 mmole) was added in a stream over 2 min to a solution of 2-(3-butynyloxy)tetrahydro-2H-pyran (4.7 mL, 30 mmole) in dry THF (60 mL) at 0° C. under argon. After 0.5 hr, tributyltin chloride (8.1 mL, 30 mmole) was added all at once, and the reaction was warmed to RT. After 3 hr, the reaction was diluted with hexanes (300 mL) and washed sequentially with H$_2$O (2×60 mL), 10% KF (2×30 mL), and saturated brine (60 mL). Drying (Na$_2$SO$_4$), concentration, and silica gel chromatography (3% EtOAc/hexanes) gave the title compound (3.58 g, 27%) as a nearly colorless oil: TLC (5% EtOAc/hexanes) R$_f$ 0.37; $^1$H NMR (400 MHz, CDCl$_3$) δ 4.66 (narrow t, 1 H), 3.75–3.96 (m, 2 H), 3.49–3.62 (m, 2 H), 2.56 (app t, 2 H), 1.76–1.91 (m, 1 H), 1.65–1.78 (m, 1H), 1.42–1.65 (m, 10 H), 1.22–1.41 (m, 6 H), 0.82–1.08 (m, 15 H).

b) Ethyl (±)-3-[4-(2-tetrahydropyranyloxy)-1-butyn-1-yl]-5H-dibenzo[a,d]cycloheptene-10-acetate A mixture of ethyl (±)-10,11-dihydro-3-(trifluoromethanesulfonyloxy)-5H-dibenzo[a,d]cycloheptene-10-acetate (1.34 g, 3.13 mmole), 4-(2-tetrahydropyranyloxy)-1-tributylstannyl-1-butyne (1.66 g, 3.76 mmole), LiCl (398 mg, 9.39 mmole), bis(triphenylphosphine)palladium dichloride (110 mg, 0.094 mmole), and anhydrous dioxane (31 mL) was heated at reflux under argon. After 1.5 hr, the reaction was concentrated to remove most of the dioxane, and the residue was taken up in Et$_2$O (100 mL). 10% KF (50 mL) was added and the mixture was stirred briskly for 0.5 hr. The aqueous layer was removed and the Et$_2$O layer was filtered through a mixture of celite® and MgSO$_4$. The filtrate was concentrated and the residue was chromatographed on silica gel (10% EtOAc/hexanes) to afford the title compound (1.12 g, 83%) as a pale yellow oil: TLC (20% EtOAc/hexanes) R$_f$ 0.40; $^1$H NMR (400 MHz, CDCl$_3$) δ 7.21–7.30 (m, 1 H), 7.06–7.20 (m, 5 H), 7.00 (d, J=7.8 Hz, 1 H), 4.69 (t, J=3.6 Hz, 1 H), 4.31 (d, J=15.2 Hz, 1H), 4.11–4.23 (m, 2 H), 3.76–3.97 (m, 4 H), 3.59–3.68 (m, 1 H), 3.48–3.57 (m, 1 H), 3.34 (dd, J=15.2, 4.1 Hz, 1H), 2.97 (dd, J=15.2, 9.5 Hz, 1 H), 2.70 (t, J=7.3 Hz, 2 H), 2.65 (dd, J=15.7, 4.8 Hz, 1 H), 2.51 (dd, J=15.7, 9.5 Hz, 1 H), 1.78–1.92 (m, 1H), 1.68–1.78 (m, 1 H), 1.44–1.68 (m, 4 H), 1.27 (t, J=7.1 Hz, 3 H); MS (ES) m/e 455 (M+Na)$^+$.

c) Ethyl (±)-3- [4- (2-tetrahydropyranyloxy)-1-butyl]-5H-dibenzo[a,d]cycloheptene-10-acetate A mixture of ethyl (±)-3-[4-(2-tetrahydropyranyloxy)-1-butyn-1-yl]-5H-dibenzo[a,d]cycloheptene-10-acetate (1.2 g, 2.77 mmole), 10% Pd/C (0.3 g, 0.28 mmole), and EtOAc (28 mL) was shaken at RT under hydrogen (50 psi) on a Parr apparatus. After 3 hr, the reaction was filtered through celite® and the filtrate was concentrated. Silica gel chromatography (10% EtOAc/hexanes) gave the title compound (1.06 g, 88%) as a colorless oil: TLC (20% EtOAc/hexanes) R$_f$ 0.51; $^1$H NMR (400 MHz, CDCl$_3$) δ 7.05–7.20 (m, 4 H), 6.92–7.03 (m, 3 H), 4.53–4.60 (m, 1 H), 4.34 (d, J=15.1 Hz, 1 Hz, 1 H), 4.12–4.26 (m, 2 H), 3.80–3.90 (m, 3 H), 3.71–3.80 (m, 1 H), 3.44–3.53 (m, 1 H), 3.35–3.44 (m, 1 H), 3.33 (dd, J=15.1, 4.1 Hz, 1 H), 2.95 (dd, J=15.1, 9.4 Hz, 1 H), 2.65 (dd, J=15.5, 4.9 Hz, 1 H), 2.49–2.61 (m, 3 H), 1.77–1.90 (m, 1 H), 1.45–1.77 (m, 9 H), 1.27 (t, J=7.1 Hz, 3 H); MS (ES) m/e 459 (M+Na)$^+$.

d) Ethyl (±)-3-[4-hydroxy-1-butyl]-5H-dibenzo[a,d]cycloheptene-10-acetate

A solution of ethyl (±)-3-[4-(2-tetrahydropyranyloxy)-1-butyl]-5H-dibenzo[a,d]cycloheptene-10-acetate (456.0 mg, 1.04 mmole) and p-toluenesulfonic acid monohydrate (60 mg, 0.31 mmole) in absolute EtOH (10 mL) was stirred at RT. After 2 hr, the reaction was quenched with 5% NaHCO$_3$ (1 mL) and concentrated to remove the EtOH. The residue was diluted with H$_2$O (2 mL) and extracted with CH$_2$Cl$_2$. Drying (MgSO$_4$), concentration, and silica gel chromatography (1:1 EtOAc/hexanes) gave the title compound (342.4 mg, 93%) as a colorless oil: TLC (1:1 EtOAc/hexanes) R$_f$ 0.49; $^1$H NMR (250 MHz, CDCl$_3$) δ 6.85–7.25 (m, 7 H), 4.34 (d, J=15.1 Hz, 1 H), 4.08–4.30 (m, 2 H), 3.75–3.95 (m, 2 H), 3.53–3.72 (m, 2 H), 3.33 (dd, J=15.1, 4.1 Hz, 1 H), 2.95 (dd, J=15.1, 9.4 Hz, 1 H), 2.40–2.75 (m, 4 H), 1.45–1.80 (m, 4 H), 1.27 (t, J=7.1 Hz, 3 H); MS (ES) m/e 353 (M+H)$^+$.

e) Ethyl (±)-3-[3-carboxy-1-propyl]-5H-dibenzo [a,d]cycloheptene-10-acetate

A solution of ethyl (±)-3-[4-hydroxy-1-butyl]-5H-dibenzo[a,d]cycloheptene-10-acetate (342.4 mg, 0.97 mmole) in anhydrous CH$_2$Cl$_2$ (19 mL) was cooled to 0° C. under argon, and 2,2,6,6-tetramethyloxopiperidinium chloride (J. Org. Chem. 1985, 50, 1332–1334; 260 mg, 1.36 mmole) was added in one portion. The reaction was stirred at 0° C. for 1 hr, then 2-methyl-2-butene (1.2 mL, 11 mmole) was added, followed by a cold (0° C.) solution of NaClO$_2$ (0.88 g, 7.76 mmole) and NaH$_2$PO$_4$ (0.90 g, 6.50 mmole) in H$_2$O (26 mL). After 10 min, the reaction was diluted with EtOAc (100 mL) and the layers were separated. The organic layer was washed sequentially with cold 1.0 N HCl (10 mL) and saturated brine (20 mL), dried (MgSO$_4$), and concentrated. Silica gel chromatography (gradient: 1:1 EtOAc/CHCl3 then 9:9:2 EtOAc/CHCl$_3$/EtOH) gave impure title compound. Rechromatography on silica gel (7:3:0.1 toluene/EtOAc/AcOH) gave the pure title compound (233.7 mg, 66%): TLC (1:1 EtOAc/CHCl$_3$) R$_f$ 0.46; $^1$H NMR (400 MHz, CDCl$_3$) δ 7.05–7.22 (m, 4 H), 6.92–7.05 (m, 3 H), 4.34 (d, J=15.0 Hz, 1 H), 4.10–4.25 (m, 2 H), 3.80–3.90 (m, 2 H), 3.33 (dd, J=15.1, 4.1 Hz, 1 H), 2.95 (dd, J=15.1, 9.4 Hz, 1 H), 2.48–2.60 (m, 4 H), 2.48–2.60 (m, 4 H), 2.37 (t, J=7.4 Hz, 2 H), 1.87–2.00 (m, 2 H), 1.27 (t, J=7.2 Hz, 3 H); MS (ES) m/e 389 (M+Na)$^+$, 367 (M+H)$^+$.

f) Ethyl (±)-3-[3-[[(2-aminophenyl)amino]carbonyl]prop-1-yl]-5H-dibenzo[a,d]cycloheptene-10-acetate A solution of ethyl (±)-3-[3-carboxy-1-propyl]-5H-dibenzo[a,d]cycloheptene-10-acetate (233.7 mg, 0.64 mmole) in dry THF (6.4 mL) was cooled to 0° C. under argon, and 4-methylmorpholine (0.14 mL, 1.28 mmole) was added. The solution was stirred at 0° C. for several min, then isobutyl chloroformate (0.11 mL, 0.83 mmole) was added dropwise. The cloudy reaction was stirred at 0° C. for 0.5 hr, then a solution of 1,2-phenylenediamine (138 mg, 1.28 mmole) in dry THF (0.6 mL) was added rapidly. The reaction was warmed to RT and stirred for 3 hr, then was diluted with H$_2$O (2 mL) and extracted with EtOAc. Drying (MgSO$_4$), concentration, and silica gel chromatography (3:2 EtOAc/hexanes) gave the title compound (257.6 mg, 88%) as a light yellow foam: TLC (3:2 EtOAc/hexanes) R$_f$ 0.40; $^1$H NMR (250 MHz, CDCl$_3$) δ 6.90–7.23 (m, 10 H), 6.72–6.80 (m, 2 H), 4.33 (d, J=15.0 Hz, 1 H), 4.10–4.25 (m, 2 H), 3.71–3.91 (m, 4 H), 3.32 (dd, J=15.1, 4.0 Hz, 1 H), 2.95 (dd, J=15.1, 9.5 Hz, 1 H), 2.59–2.72 (m, 3 H), 2.54 (dd, J=15.6,9.5 Hz, 1 H), 2.34 (t, J=7.4 Hz, 2 H), 1.98–2.09 (m, 2 H), 1.27 (t, J=7.1 Hz, 3 H); MS (ES) m/e 457 (M+H)$^+$.

g) Ethyl(±)-10,11-dihydro-3-[3-(2-benzimidazolyl)-1-propyl]-5H-dibenzo[a,d]cycloheptene-10-acetate A solution of ethyl (±)-3-[3-[[(2-aminophenyl)amino]carbonyl]prop-1-yl]-5H-dibenzo[a,d]cycloheptene-10-acetate (257.6 mg, 0.56 mmole) in glacial AcOH (2.8 mL) and dry THF (2.8 mL) was heated at reflux under argon. After 3 hr, the reaction was concentrated and the residue was reconcentrated from xylenes. The resulting residue was taken up in Et$_2$O (30 mL) and washed sequentially with 1.0 N NaOH (2 mL), H$_2$O (2 mL), and saturated brine (2 mL). Drying (MgSO$_4$), concentration, and silica gel chromatography (2% EtOH in 1:1 EtOAc/hexanes) gave the title compound (236.3 mg, 96%) as an off-white foam: TLC (2% EtOH in 1:1 EtOAc/hexanes) R$_f$ 0.34; $^1$H NMR (400 MHz, CDCl$_3$) δ 7.30–7.80 (m, 2 H), 7.03–7.24 (m, 6 H), 6.80–6.95 (m, 3 H), 412–428 (m, 3 H), 3.77–3.89 (m, 1 H), 3.74 (d, J=15.1 Hz, 1 H), 3.28 (dd, J=15.2, 4.0 Hz, 1 H), 2.90 (dd, J=15.2, 9.5 Hz, 1 H), 2.84 (t, J=7.7 Hz, 2 H), 2.65 (dd, J=15.7, 4.9 Hz, 1 H), 2.60 (t, J=7.5 Hz, 2 H), 2.52 (dd, J=15.7, 9.6 Hz, 1 H), 2.03–2.18 (m, 2 H), 1.28 (t, J=7.1 Hz, 3 H); MS (ES) m/e 439 (M+H)$^+$.

h) (±)-10,11-dihydro-3-[3-(2-benzimidazolyl)-1-propyl]-5H-dibenzo[a,d]cycloheptene-10-acetic acid, sodium salt A mixture of ethyl (±)-10,11-dihydro-3-[3-(2-benzimidazolyl)-1-propyl]-5H-dibenzo[a,d]cycloheptene-10-acetate (236.3 mg, 0.54 mmole), 1.0 N NaOH (0.65 mL, 0.65 mmole), and absolute EtOH (4.8 mL) was warmed in an oil bath preset at 50° C. After 16 hr, the reaction was concentrated to dryness and the residue was purified by ODS chromatography (gradient: 35% MeOH/H$_2$O, then 40% MeOH/H$_2$O). Concentration followed by lyophilization gave the title compound (143 mg, 58%) as a colorless powder: HPLC (PRP-1®, 40% CH$_3$CN/H$_2$O containing 0.1% TFA) K'=1.5; $^1$H NMR (400 MHz, CD$_3$OD) δ

7.41–7.49 (m, 2 H), 6.86–7.27 (m, 9 H), 4.24 (d, J=14.7 Hz, 1 H), 3.87 (d, J=14.7 Hz, 1 H), 3.73–3.85 (m, 1 H), 3.23–3.25 (m, 1 H, partially obscured by residual solvent signal), 2.80–2.93 (m, 3 H), 2.62 (t, J=7.5 Hz, 2 H), 2.56 (dd, J=14.4, 5.1 Hz, 1 H), 2.40 (dd, J=14.4, 9.7 Hz, 1 H), 2.05–2.17 (m, 2 H); MS (ES) m/e 411 (M+H)$^+$. Anal. Calcd for $C_{27}H_{25}N_2O_2Na$. 1.5 $H_2O$: C, 70.57; H, 6.14; N, 6.10. Found: C, 70.65; H, 5.95; N, 5.95.

EXAMPLE 4

Preparation of (±)-10,11-dihydro-3-[[[2-(2-pyridylamino)ethyl]amino]carbonyl]-5H-dibenzo[a,d]cycloheptene-10-acetic acid a) Ethyl (±)-10,11-dihydro-3-[[[2-(2-pyridylamino)ethyl]amino]carbonyl]-5H-dibenzo[a,d]cycloheptene-10-acetate EDC (112.7 mg, 0.59 mmole) was added all at once to a solution of ethyl (±)-10,11-dihydro-3-carboxy-5H-dibenzo[a,d]cycloheptene-10-acetate (157.8 mg, 0.49 mmole), 2-[(2-aminoethyl)amino]pyridine dihydrochloride (123.5 mg, 0.59 mmole), HOBt.$H_2O$ (79.5 mg, 0.59 mmole), and diisopropylethylamine (0.43 mL, 2.45 mmole) in anhydrous DMF (2.5 mL) at RT. The reaction was stirred at RT for 18 hr, then was concentrated. The residue was reconcentrated from xylenes, then was diluted with $H_2O$ (5 mL) and extracted sequentially with EtOAc (2×5 mL) and $CHCl_3$ (2×5 mL). The organic layers were combined and treated with a little MeOH to dissolve a small amount of insoluble material. Drying ($MgSO_4$), concentration, and silica gel chromatography (5% MeOH/$CHCl_3$) gave the title compound (199.1 mg, 92%) as a yellow oil: TLC (5% MeOH/$CHCl_3$) $R_f$ 0.42; $^1$H NMR (400, $CDCl_3$) δ 8.10 (d, J=3.5 Hz, 1 H), 8.02 (br s, 1 H), 7.60 (app. narrow d, 1 H), 7.53 (app. dd, 1 H), 7.33–7.42 (m, 1 H), 7.08–7.22 (m, 5 H), 6.57–6.65 (m, 1 H), 6.45 (d, J=8.3 Hz, 1 H), 4.79–4.90 (m, 1 H), 4.36 (d,J=15.1 Hz, 1 H), 4.11–4.26 (m, 2 H), 3.92 (d, J=15.1 Hz, 1 H), 3.80–3.95 (m, 1 H), 3.55–3.72 (m, 4 H), 3.38 (dd, J=15.2, 4.1 Hz, 1 H), 3.03 (dd, J=15.2, 9.5 Hz, 1 H), 2.66 (dd, J=15.8,4.8 Hz, 1 H), 2.50 (dd, J=15.8, 9.6 Hz, 1 H), 1.27 (t, J=7.2 Hz, 3 H); MS (ES) m/e 444 (M+H)$^+$.

b) (±)-10,11-Dihydro-3-[[[2-(2-pyridylamino)ethyl]amino]carbonyl]-5H-dibenzo[a,d]cycloheptene-10-acetic acid, sodium salt A solution of ethyl (±)-10,11-dihydro-3-[[[2-(2-pyridylamino)ethyl]amino]carbonyl]-5H-dibenzo[a,d]cycloheptene-10-acetate (199.1 mg, 0.45 mmole) and 1.0 N NaOH (0.54 mL, 0.54 mmole) in absolute EtOH (4 mL) was warmed in an oil bath set at 45° C. After 23 hr, the reaction was concentrated and the residue was purified by ODS chromatography (gradient: 30% MeOH/$H_2O$ then 40% MeOH/$H_2O$). Concentration and lyophilization gave the title compound (95.8 mg, 46%) as a nearly colorless powder: HPLC (PRP-1®, 30% $CH_3CN/H_2O$ containing 0.1% TFA) K' =2.0; $^1$H NMR (400 MHz, $CD_3OD$) δ 7.92 (app. d, J=4.2 Hz, 1 H), 7.61 (d, J=1.8 Hz, 1 H), 7.53 (dd, J=7.9, 1.8 Hz, 1 H), 7.38–7.47 (m, 1 H), 7.01–7.24 (m, 5 H), 6.56 (d, J=7.9 Hz, 1 H), 6.50–6.60 (m, 1 H), 4.34 (d, J=14.9 Hz, 1 H), 3.97 (d, J=14.9 Hz, 1 H), 3.78–3.89 (m, 1 H), 3.44–3.61 (m, 4 H), 3.39 (dd, J=15.4, 4.4 Hz, 1 H), 3.00 (dd, J=15.4, 10.2 Hz, 1 H), 2.61 (dd, J=14.9, 5.1 Hz, 1 H), 2.43 (dd, J=14.9, 9.5 Hz, 1 H); MS (ES) m/e 416 (M+H)$^+$. Anal. Calcd for $C_{25}H_{24}N_3O_3Na$.1.33 $H_2O$: C, 65.07; H, 5.82; N, 9.11. Found: C, 65.02; H, 5.62; N, 9.17.

EXAMPLE 5

Preparation of (±)-10,11-dihydro-3-[3-(2-pyridylamino)-1-propyloxy]-5H-dibenzo[a,d]cycloheptene-10-acetic acid a) Ethyl (±)-10,11-dihydro-3-[3-[2-(N-oxopyridyl)amino]-1-propyloxy]-5H-dibenzo[a,d]cycloheptene-10-acetate A solution of 2-[(3-hydroxy-1-propyl)amino]pyridine-N-oxide (2 mmole) and diethyl azodicarboxylate (2 mmole) in anhydrous DMF (10 mL) is added slowly dropwise to a solution of ethyl (±)-10,11-dihydro-3-hydroxy- 5H-dibenzo[a,d]cycloheptene-10-acetate (1 mmole) and triphenylphosphine (2.1 mmole) in anhydrous DMF (10 mL) at RT under argon. When the reaction is complete, the solvents are removed on the rotavap, and the residue is reconcentrated from xylenes to remove residual DMF. Silica gel chromatography affords the title compound.

b) Ethyl (±)-10,11-dihydro-3-[3-(2-pyridylamino)-1-propyloxy]-5H-dibenzo[a,d]cycloheptene-10-acetate A mixture of ethyl (±)-10,1 1-dihydro-3-[3-[2-(N-oxopyridyl)amino]-1-propyloxy]-5H-dibenzo[a,d]cycloheptene-10-acetate (1 mmole), cyclohexene (10 mmole), and 10% Pd/C (0.1 mmole) in isopropanol (10 mL) is heated at reflux. When the reaction is complete, the mixture is filtered through celite®, and the filtrate is concentrated on the rotavap. The residue is reconcentrated from toluene, then is chromatographed on silica gel to afford the title compound.

c) (±)-10,11-Dihydro-3-[3-(2-pyridylamino)-1-propyloxy]-5H-dibenzo[a,d]cycloheptene-10-acetic acid, sodium salt A mixture of ethyl (±)-10,11-dihydro-3-[3-(2-pyridylamino)-1-propyloxy]-5H-dibenzo[a,d]cycloheptene-10-acetate (1 mmole) and 1.0 N NaOH (1.2 mmole) in absolute EtOH (10 mL) is warmed in an oil bath set at 50° C. When the reaction is complete, the solvents are removed on the rotavap and the residue is purified by ODS chromatography. Concentration and lyophilization afford the title compound.

EXAMPLE 6

2-[[[(1 H-Benzimidazol-2-yl)methyl]methylamino]carbonyl]-6,11-dihydro-5H-dibenz[b,e]azepine-6-acetic Acid a) Methyl 2-[[[(1 H-benzimidazol-2-yl)methyl]methylamino]carbonyl]-6,11-dihydro-5H-dibenz[b,e]azepine-6-acetate Using the procedure of Example 1(a), except substituting the compound of Preparation 16(d) for the compound of Preparation 1(i), gives the title compound.

b) 2-[[[(1 H-Benzimidazol-2-yl)methyl]methylamino]carbonyl]-6,11-dihydro-5H-dibenz[b,e]azepine-6-acetic Acid Using the procedure of Example 1(b), except substituting the compound of Example 6(a) for the compound of Example 1(a), gives the title compound.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

$$\text{(I)}$$

wherein $A_1$ is C;

E is a six-membered aromatic carbocyclic ring optionally substituted by $R^3$ or $R^4$;

$X^1$—$X^2$ is CHR$^1$—CH, CR$^1$=CH, NR$^1$—CH, S(O)$_u$—CH or O—CH;

$X^3$ is CR$^5$R$'^5$, NR$^5$, S(O)$_u$ or O;

R' is H, $C_{1-6}$alkyl, $C_{3-7}$cycloalkyl-$C_{0-4}$alkyl or Ar-$C_{0-4}$alkyl;

R" is R', —C(O)R' or —C(O)OR$^5$;

R'" is $C_{1-6}$alkyl, $C_{3-7}$cycloalkyl-$C_{0-4}$alkyl or Ar-$C_{1-4}$alkyl;

$R^1$ is H, $C_{1-6}$alkyl, $C_{3-7}$cycloalkyl-$C_{0-4}$alkyl or Ar-$C_{0-4}$alkyl;

$R^2$ is —OR', —NR'R", —NR'SO$_2$R'", —NR'OR', —OCR'$_2$C(O)OR', —OCR'$_2$OC(O)—R', —OCR'$_2$C(O)NR'$_2$, CF$_3$ or —COCR'$_2$R$^{2'}$;

$R^{2'}$ is —OR', —CN, —S(O)$_r$R', S(O)$_2$NR'$_2$, —C(O)R' C(O)NR'$_2$ or —CO$_2$R';

$R^5$ and $R^{5'}$ are independently H, $C_{1-6}$alkyl, $C_{3-7}$cycloalkyl-$C_{0-4}$alkyl or Ar-$C_{0-4}$alkyl;

$R^6$ is W—(CR'$_2$)$_q$—Z—(CR'R$^{10}$)$_r$—U—(CR'$_2$)$_s$—V— or W'—(CR'$_2$)$_q$—U—(CR'$_2$)$_s$—;

$R^3$, $R^4$ and $R^7$ are independently H, halo, —OR$^{12}$, —SR$^{12}$, —CN, —NR'R$^{12}$, —NO$_2$, —CF$_3$, CF$_3$S(O)$_r$—, —CO$_2$R', —CONR'$_2$, R$^{14}$—$C_{0-6}$alkyl-, R$^{14}$—$C_{1-6}$oxoalkyl-, R$^{14}$—$C_{2-6}$alkenyl-, R$^{14}$—$C_{2-6}$alkynyl, R$^{14}$—$C_{0-6}$alkyloxy-, R$^{14}$—$C_{0-6}$alkylamino or R$^{14}$—$C_{0-6}$alkyl-S(O)$_r$—;

$R^8$ is R', C(O)R', CN, NO$_2$, SO$_2$R' or C(O)OR$^5$;

$R^9$ is R', —CF$_3$, —SR', or —OR';

$R^{10}$ is H, $C_{1-4}$alkyl or —NR'R";

$R^{12}$ is R', —C(O)R', —C(O)NR'$_2$, —C(O)OR$^5$, —S(O)$_m$R' or S(O)$_2$NR'$_2$;

$R^{14}$ is H, $C_{3-6}$cycloalkyl, Het or Ar;

$R^{15}$ is H, $C_{1-10}$alkyl, $C_{3-7}$cycloalkyl-$C_{0-8}$alkyl or Ar-$C_{0-8}$alkyl;

U and V are absent or CO, CR'$_2$, C(=CR$^{15}_2$), S(O)$_n$, O, NR$^{15}$, CR$^{15}$,OR$^{15}$, CR'(OR")CR'$_2$, CR'$_2$CR'(OR"), C(O)CR'$_2$, CR$^{15}_2$C(O), CONR$^{15}$, NR$^{15}$CO, OC(O), C(O)O, C(S)O, OC(S), C(S)NR$^{15}$, NR$^{15}$C(S), SO$_2$NR$^{15}$, NR$^{15}$SO$_2$, N=N, NR$^{15}$NR$^{15,}$ $^{NR15}$CR$^{15}_2$, NR$^{15}$CR$^{15}_2$O, CR$^{15}_2$O, OCR$^{15}_2$, C≡C, CR$^{15}$=CR$^{15}$, Het, or Ar provided that U and V are not simultaneously absent;

W is R'R"N—, R'R"NR'N—, R'R"NR'NCO—, R'$_2$NR'NC(=NR')—, R'ONR'C(=NR')—,

Q is NR',O or S;

$R^a$ is H, $C_{1-6}$alkyl, Ar-$C_{0-6}$alkyl, Het-$C_{0-6}$alkyl, or $C_{3-6}$cycloalkyl-$C_{0-6}$alkyl, halogen, OR$^1$, SR$^1$, COR$^1$, OH, NO$_2$, N(R$^1$)$_2$, CO(NR$^1$)$_2$, CH$_2$N(R$^1$)$_2$;

$R^b$ and $R^c$ are independently selected from H, $C_{1-6}$ alkyl, Ar-$C_{1-6}$alkyl, Het-$C_{0-6}$alkyl, or $C_{3-6}$cycloalkyl-$C_{0-6}$alkyl, halogen, OR$^1$, SR$^1$, COR$^1$, OH, NO$_2$, N(R$^1$)$_2$, CO(NR$^1$)$_2$, CH$_2$N(R$^1$)$_2$, or $R_b$ and $R_c$ are joined together to form a five or six membered aromatic or non-aromatic ring, optionally substituted by halogen, $C_{1-4}$alkyl, OR$^1$, SR$^1$, COR$^1$, OH, NO$_2$, N(R$^1$)$_2$, CO(NR$^1$)$_2$, CH$_2$N(R$^1$)$_2$, CN, or R"R'NC(=NR')—;

X is N=CR', C(O) or O;

Y is absent, S or O;

Z is (CH$_2$)$_t$, Het, Ar or $C_{3-7}$cycloalkyl;

m is 1 or 2;

n is 0, 1, 2 or 3;

q is 0, 1, 2 or 3;

r is 0, 1 or 2;

s is 0, 1 or 2;

t is 0, 1 or 2;

u is 0, 1 or 2;

v is 0 or 1; and w is 0 or 1; or a pharmaceutically acceptable salt thereof.

2. A compound according to claim 1 wherein $R^6$ is chosen from:

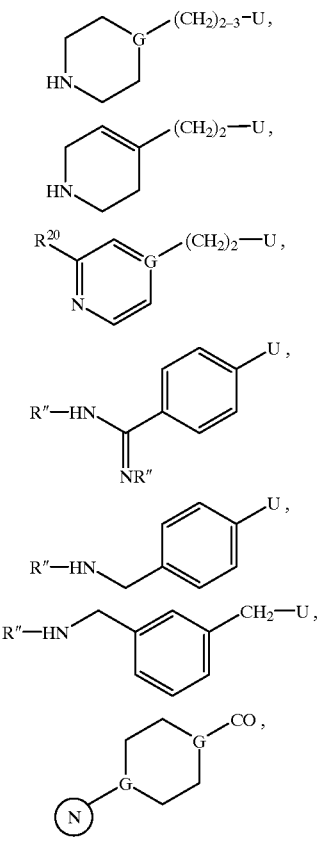

R"HNC(=NH)NH—(CH$_2$)$_3$(CHR$^{10}$)—U, and R"HN—(CH$_2$)$_5$—U wherein G is N or CH, $R^{20}$ is hydrogen, amino, mono-C$_{1-4}$alkylamino, or di-C$_{1-4}$alkylamino, hydroxy or C$_{1-4}$alkyl, and U is NR$^{15}$CO, CONR$^{15}$, (CH$_2$)CO, CH=CH, C≡C, CH$_{2O}$, or OCH$_2$.

3. A compound according to claim 1 wherein $R^6$ is W'-(CR'$_2$)$_q$—U—, and
W' is

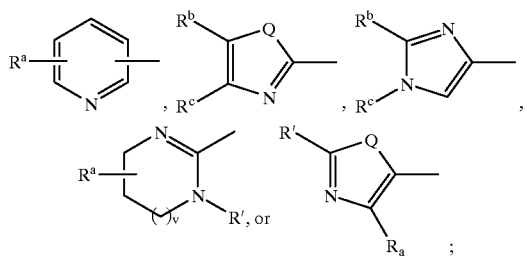

Q is NH;

$R^a$ is C$_{1-6}$alkyl, C$_{1-6}$alkoxy, halogen or R'NH;

$R^b$ and $R^c$ are joined to form an optionally substituted cyclohexyl, phenyl or pyridyl ring, and U— is NR$^{16}$CO, CH$_2$O or CH$_2$.

4. A compound according to claim 1 which is:

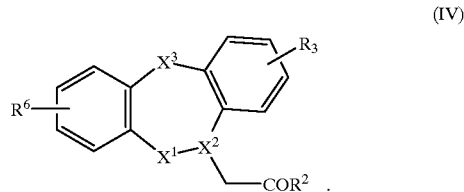

(IV)

5. A compound according to claim 4, wherein $X^1$–$X^2$ is CH$_2$—CH or NH—CH and $X^3$ is CH$_2$.

6. A compound according to claim 1 which is:

(±)-10,11-Dihydro-3-[[[(1 H-benzimidazole-2-yl)methyl]methylamino]carbonyl]-5H-dibenzo[a,d]cycloheptene-10-acetic acid;

(±)-10,11-Dihydro-3-[1-(4,4'-bipiperidinyl)carbonyl]-5H-dibenzo[a,d]cycloheptene-10-acetic acid;

(±)-10,11-Dihydro-3-[3-(2-benzimidazolyl)-1-propyl]-5H-dibenzo[a,d]cycloheptene-10-acetic acid;

(±)-10,11-Dihydro-3-[[[2-(2-pyridylamino)ethyl]amino]carbonyl]-5H-dibenzo[a,d]cycloheptene-10-acetic acid;

(±)-10,11-Dihydro-3-[3-(2-pyridylamino)-1-propyloxy]-5H-dibenzo[a,d]cycloheptene-10-acetic acid; or 2-[[[(1 H-Benzimidazol-2-yl)methyl]methylamino]carbonyl]-6,11-dihydro-5H-dibenz[b,e]azepine-6-acetic acid.

7. A pharmaceutical composition comprising an effective amount of a compound according to claim 1 and a pharmaceutically acceptable carrier.

8. A method of inhibiting the fibrinogen receptor comprising administering a compound according to claim 1.

9. A method of inhibiting a vitronectin receptor comprising administering a compound according to claim 1.

10. A method for treating osteoporosis, atherosclerosis, cancer or restenosis following angioplasty in a mammal comprising administering a compound according to claim 1 and a pharmaceutically acceptable carrier.

11. A method of treating stroke, transient ischemia attacks, myocardial infarction or inhibiting reocclusion following thrombolytic therapy comprising administering a compound according to claim 1 and a pharmaceutically acceptable carrier.

* * * * *